US009839451B2

(12) United States Patent
Sturm et al.

(10) Patent No.: US 9,839,451 B2
(45) Date of Patent: Dec. 12, 2017

(54) FACET JOINT REPLACEMENT DEVICE AND METHODS OF USE

(71) Applicants: Christopher D. Sturm, Milton, WI (US); Shawn Van Dahm, Bolingbrook, IL (US)

(72) Inventors: Christopher D. Sturm, Milton, WI (US); Shawn Van Dahm, Bolingbrook, IL (US)

(*) Notice: Subject to any disclaimer, the term of this patent is extended or adjusted under 35 U.S.C. 154(b) by 0 days.

(21) Appl. No.: 15/472,021

(22) Filed: Mar. 28, 2017

(65) Prior Publication Data

US 2017/0281248 A1 Oct. 5, 2017

Related U.S. Application Data

(60) Provisional application No. 62/314,634, filed on Mar. 29, 2016.

(51) Int. Cl.
*A61F 2/44* (2006.01)
*A61B 17/70* (2006.01)
*A61B 17/84* (2006.01)

(52) U.S. Cl.
CPC ...... *A61B 17/7064* (2013.01); *A61B 17/7058* (2013.01); *A61B 17/84* (2013.01)

(58) Field of Classification Search
CPC . A61B 17/7064; A61B 17/7058; A61B 17/84; A61B 17/7067; A61B 17/7049;
(Continued)

(56) References Cited

U.S. PATENT DOCUMENTS 5,571,191 A  11/1996 Fitz
6,132,464 A  10/2000 Martin
(Continued)

FOREIGN PATENT DOCUMENTS

DE  10135771 A1  2/2003
DE  102007038996 A1  4/2009
(Continued)

OTHER PUBLICATIONS

International Search Report dated Jun. 22, 2017 in Application No. PCT/US2017/024591, filed on Mar. 28, 2017.

*Primary Examiner* — Pedro Philogene
(74) *Attorney, Agent, or Firm* — Knobbe, Martens, Olson & Bear, LLP

(57) ABSTRACT

A facet joint replacement device includes an enclosing element including an enclosing body and an inferior attachment member. The enclosing body includes an inner cavity defined by an interior surface of the enclosing body, wherein a portion of the interior surface of the enclosing body forms a superior articulating surface. The facet joint replacement device also includes an inferior articulating element including an articulating body and a superior attachment member. The inferior articulating body is positioned within the inner cavity of the enclosing body of the enclosing element and is configured to move within the inner cavity of the enclosing body of the enclosing element. The inferior articulating body includes an inferior articulating surface. The movement of the articulating body of the inferior articulating element is constrained in at least one direction within the inner cavity of the enclosing body of the enclosing element.

31 Claims, 20 Drawing Sheets

(58) Field of Classification Search
CPC ............ A61B 17/8625; A61B 17/8695; A61B
2017/8655; A61F 2/4405; A61F 2/442;
A61F 2/4425; A61F 2/30771; A61F
2/4611; A61F 2002/30016; A61F
2002/30331; A61F 2002/30448; A61F
2002/30471; A61F 2002/30474; A61F
2002/30485; A61F 2002/30512; A61F
2002/3055; A61F 2002/30576; A61F
2002/30601; A61F 2002/30649; A61F
2002/30654; A61F 2002/30154; A61F
2002/30156; A61F 2002/30171; A61F
2002/30426; A61F 2002/30433; A61F
2002/30514; A61F 2002/30578; A61F
2002/30579; A61F 2002/30616; A61F
2002/30841; A61F 2002/3085; A61F
2220/0025; A61F 2220/0033; A61F
2220/005; A61F 2220/0041; A61F
2310/00017; A61F 2310/00023; A61F
2310/00029; A61F 2310/00131; A61F
2310/00203; A61F 2310/000239; A61F
2310/00796; A61F 2230/0008; A61F
2230/0021; A61F 2230/0023; A61F
2230/005
USPC ......... 623/17.11–17.16; 606/246–279, 86 A,
606/86 R
See application file for complete search history.

(56) References Cited

U.S. PATENT DOCUMENTS

| | | | |
|---|---|---|---|
| 6,419,703 B1 | 7/2002 | Fallin et al. | |
| 6,565,605 B2 | 5/2003 | Goble et al. | |
| 6,579,319 B2 | 6/2003 | Goble et al. | |
| 6,610,091 B1 | 8/2003 | Reiley | |
| 6,811,567 B2 | 11/2004 | Reiley | |
| 6,974,478 B2 | 12/2005 | Reiley | |
| 7,074,238 B2 | 7/2006 | Stinson et al. | |
| 7,090,698 B2 | 8/2006 | Goble et al. | |
| 7,101,398 B2 | 9/2006 | Dooris et al. | |
| 7,338,527 B2 | 3/2008 | Blatt et al. | |
| 7,377,942 B2 | 5/2008 | Berry | |
| 7,537,611 B2 | 5/2009 | Lee | |
| 7,588,590 B2 | 9/2009 | Chervitz et al. | |
| 7,591,851 B2 | 9/2009 | Winslow et al. | |
| 7,601,170 B2 | 10/2009 | Winslow et al. | |
| 7,608,104 B2 | 10/2009 | Yuan et al. | |
| 7,635,389 B2 | 12/2009 | Yu et al. | |
| 7,655,044 B2 | 2/2010 | Kwak | |
| 7,662,183 B2 | 2/2010 | Haines | |
| 7,674,293 B2 | 3/2010 | Kuiper et al. | |
| 7,691,145 B2 | 4/2010 | Reiley et al. | |
| 7,695,514 B2 | 4/2010 | Kwak | |
| 7,722,647 B1 | 5/2010 | Wang et al. | |
| 7,763,050 B2 | 7/2010 | Winslow et al. | |
| 7,776,090 B2 | 8/2010 | Winslow et al. | |
| 7,803,189 B2 | 9/2010 | Koske | |
| 7,811,326 B2 | 10/2010 | Braddock, Jr. et al. | |
| 7,846,183 B2 | 12/2010 | Blain | |
| 7,846,184 B2 | 12/2010 | Sasso et al. | |
| 7,862,589 B2 | 1/2011 | Thramann | |
| 7,896,903 B2 | 3/2011 | Link | |
| 7,922,766 B2 | 4/2011 | Grob et al. | |
| 7,935,136 B2 | 5/2011 | Alamin et al. | |
| 7,947,063 B2 | 5/2011 | Arnin | |
| 7,988,712 B2 | 8/2011 | Hale et al. | |
| 7,993,373 B2 | 8/2011 | Hoy et al. | |
| 7,998,176 B2 | 8/2011 | Culbert | |
| 8,029,540 B2 | 10/2011 | Winslow et al. | |
| 8,066,749 B2 | 11/2011 | Winslow et al. | |
| 8,070,783 B2 | 12/2011 | Kwak | |
| 8,118,838 B2 | 2/2012 | Winslow et al. | |
| 8,128,660 B2 | 3/2012 | Mitchell et al. | |
| 8,172,877 B2 | 5/2012 | Winslow et al. | |
| 8,182,512 B2 | 5/2012 | Muhanna | |
| 8,246,684 B2 * | 8/2012 | Lee ...................... | A61F 2/4405 623/17.15 |
| 8,409,254 B2 | 4/2013 | Yuan et al. | |
| 8,460,341 B2 | 6/2013 | Chin et al. | |
| 8,491,634 B2 | 7/2013 | Sasso et al. | |
| 8,496,686 B2 | 7/2013 | Berg et al. | |
| 8,556,936 B2 | 10/2013 | Goble et al. | |
| 8,702,755 B2 | 4/2014 | Ralph et al. | |
| 8,764,801 B2 | 7/2014 | Chervitz et al. | |
| 8,840,647 B2 | 9/2014 | Siemionow et al. | |
| 9,056,016 B2 | 6/2015 | Reiley et al. | |
| 9,084,638 B2 | 7/2015 | Linares | |
| 9,089,436 B2 | 7/2015 | Overes et al. | |
| 9,198,767 B2 | 12/2015 | Abdou | |
| 9,314,277 B2 | 4/2016 | Assell et al. | |
| 9,339,394 B2 | 5/2016 | Chervitz et al. | |
| 2003/0028254 A1 * | 2/2003 | Hunter ................... | A61L 27/16 623/20.21 |
| 2004/0230201 A1 | 11/2004 | Yuan et al. | |
| 2005/0027361 A1 | 2/2005 | Reiley | |
| 2005/0033434 A1 * | 2/2005 | Berry .................. | A61B 17/7064 623/17.14 |
| 2005/0197700 A1 | 9/2005 | Boehm, Jr. et al. | |
| 2005/0261770 A1 | 11/2005 | Kuiper et al. | |
| 2005/0267579 A1 | 12/2005 | Reiley | |
| 2006/0247633 A1 | 11/2006 | Winslow et al. | |
| 2006/0247650 A1 | 11/2006 | Yerby et al. | |
| 2006/0265074 A1 * | 11/2006 | Krishna ............. | A61B 17/7014 623/17.15 |
| 2006/0276790 A1 | 12/2006 | Dawson et al. | |
| 2007/0016196 A1 | 1/2007 | Winslow et al. | |
| 2007/0016297 A1 | 1/2007 | Johnson | |
| 2007/0055373 A1 | 3/2007 | Hudgins et al. | |
| 2007/0073290 A1 | 3/2007 | Boehm, Jr. | |
| 2007/0088358 A1 | 4/2007 | Yuan et al. | |
| 2007/0093833 A1 | 4/2007 | Kuiper et al. | |
| 2007/0179617 A1 | 8/2007 | Brown et al. | |
| 2007/0198091 A1 | 8/2007 | Boyer et al. | |
| 2007/0233256 A1 | 10/2007 | Ohrt et al. | |
| 2008/0027547 A1 | 1/2008 | Yu et al. | |
| 2008/0177310 A1 | 7/2008 | Reiley | |
| 2008/0177311 A1 | 7/2008 | Winslow et al. | |
| 2008/0183209 A1 | 7/2008 | Robinson et al. | |
| 2008/0319483 A1 * | 12/2008 | Triplett ................. | A61F 2/4405 606/246 |
| 2012/0221049 A1 * | 8/2012 | Blain ................. | A61B 17/7053 606/247 |
| 2014/0277140 A1 | 9/2014 | Jarolem | |
| 2014/0288601 A1 | 9/2014 | Baynham | |
| 2015/0230833 A1 | 8/2015 | Chervitz et al. | |
| 2015/0230933 A1 | 8/2015 | Fallin et al. | |
| 2015/0342648 A1 | 12/2015 | McCormack et al. | |

FOREIGN PATENT DOCUMENTS

| | | |
|---|---|---|
| DE | 102007051782 A1 | 5/2009 |
| FR | 2832054 | 5/2003 |
| WO | WO 2005/048876 A2 | 6/2005 |

* cited by examiner

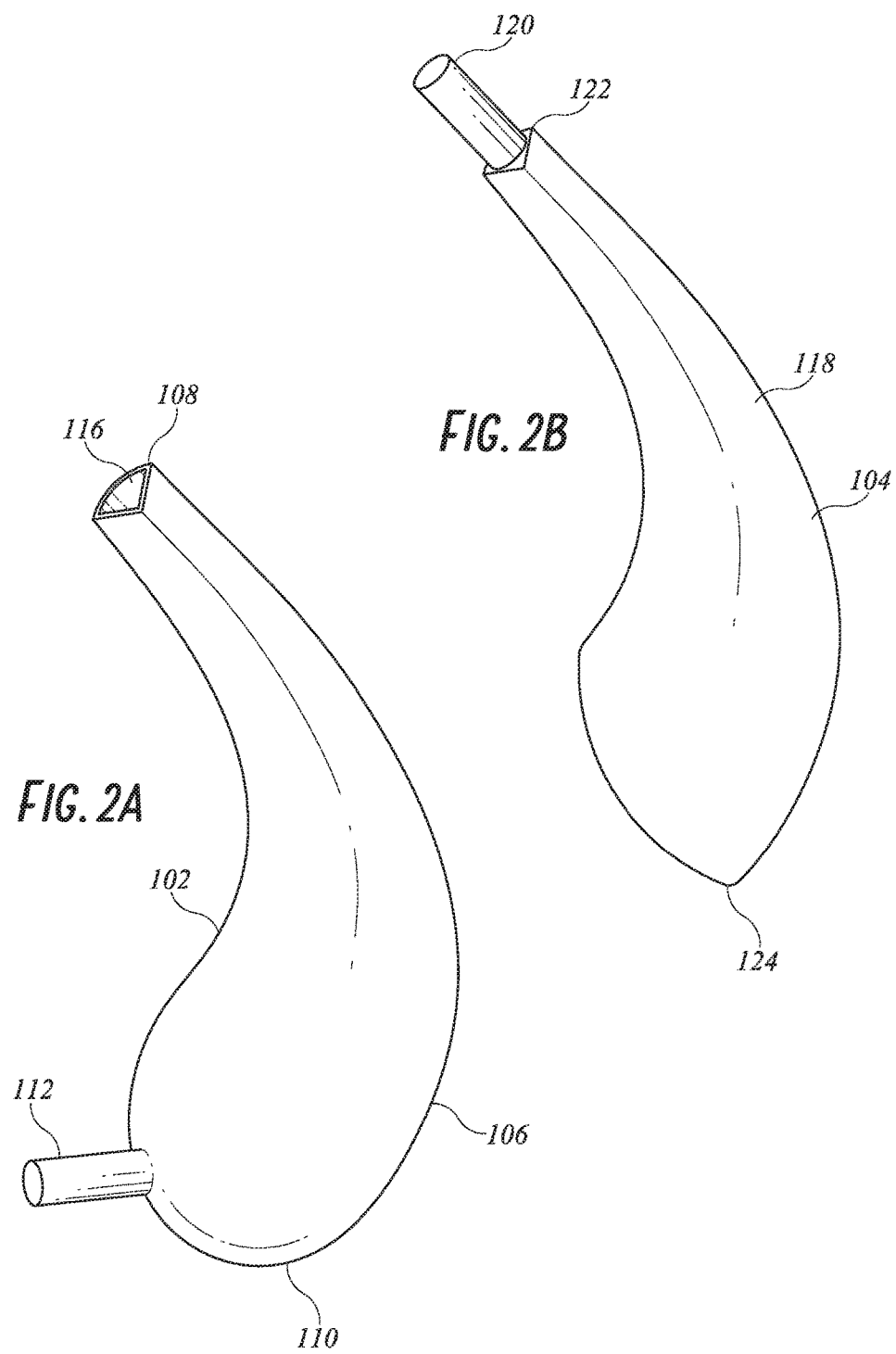

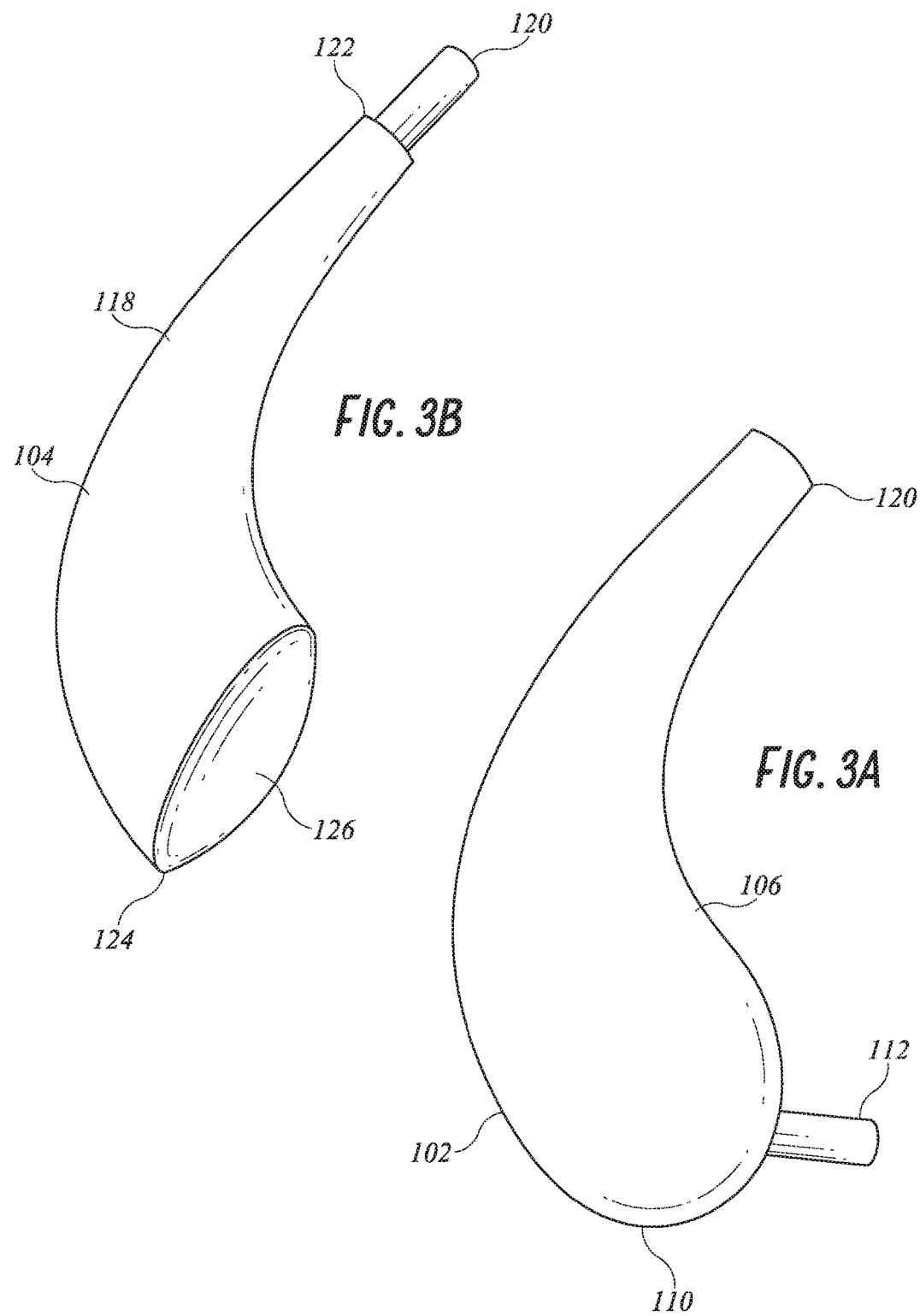

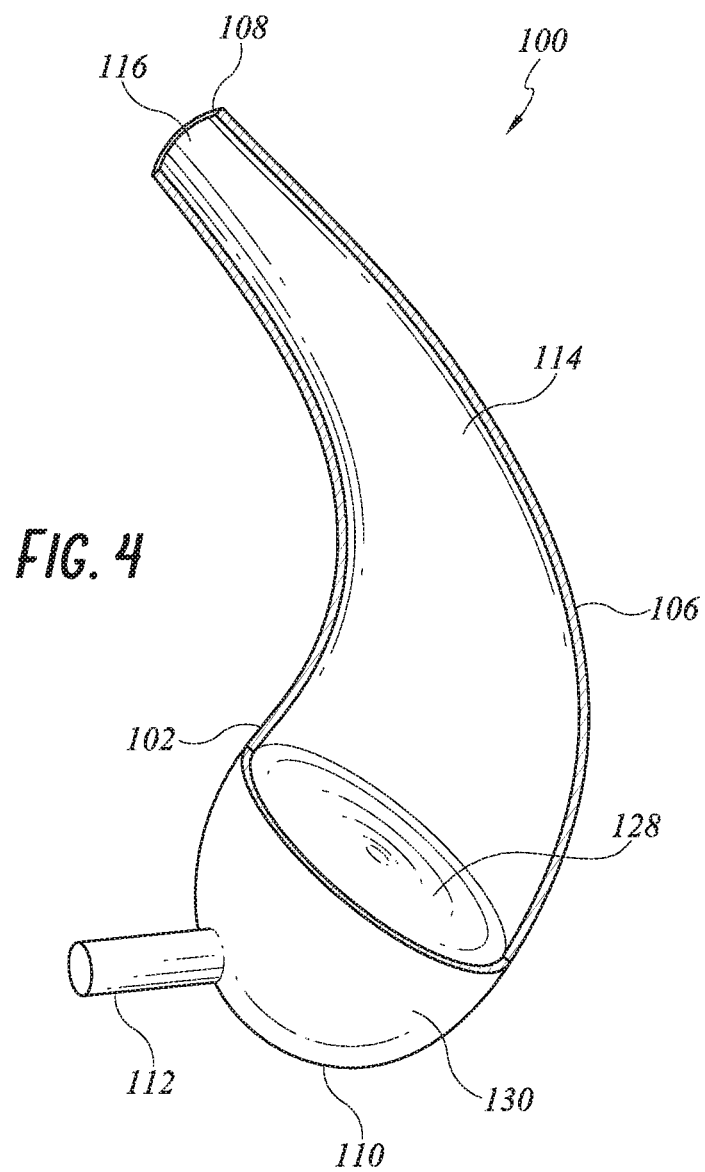

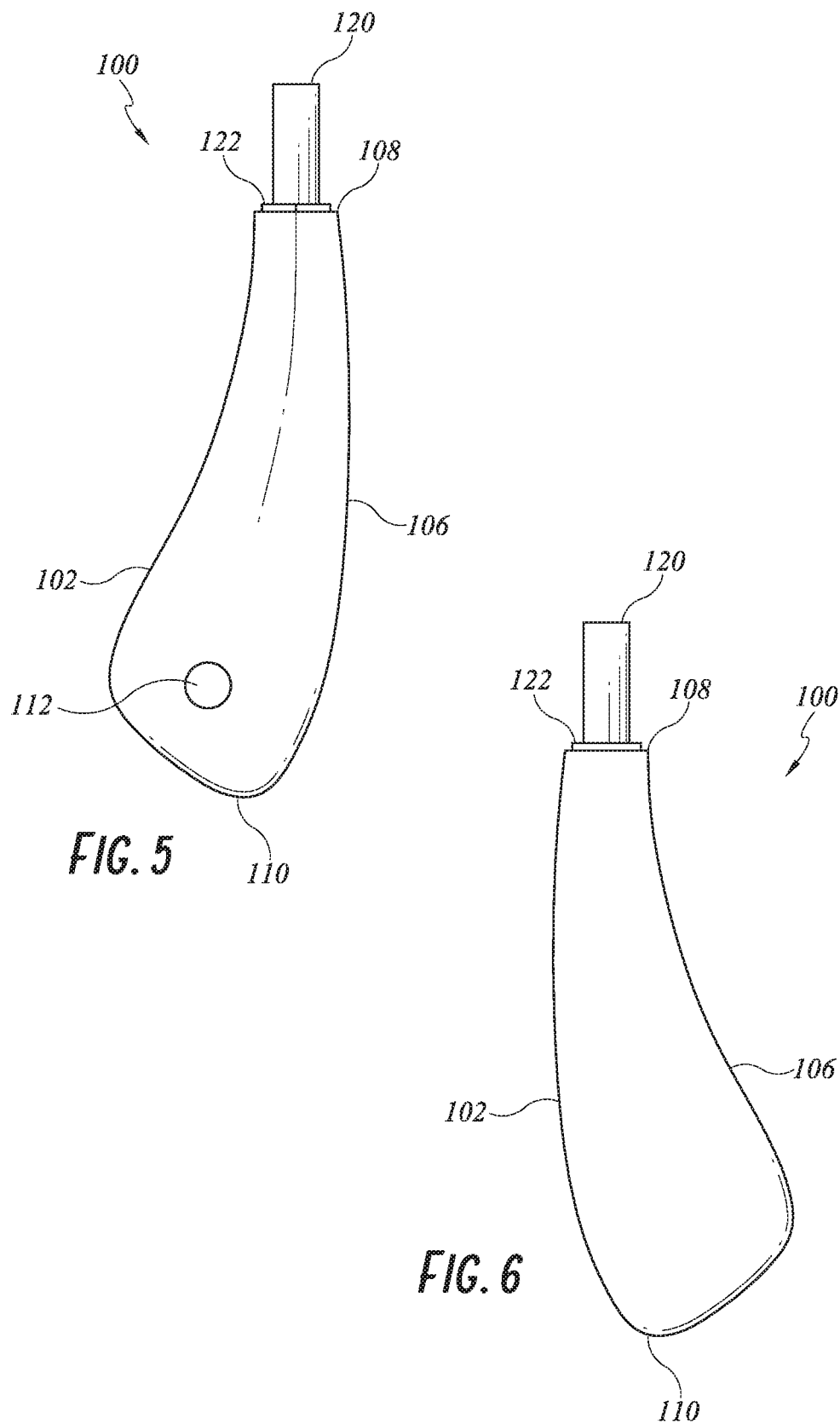

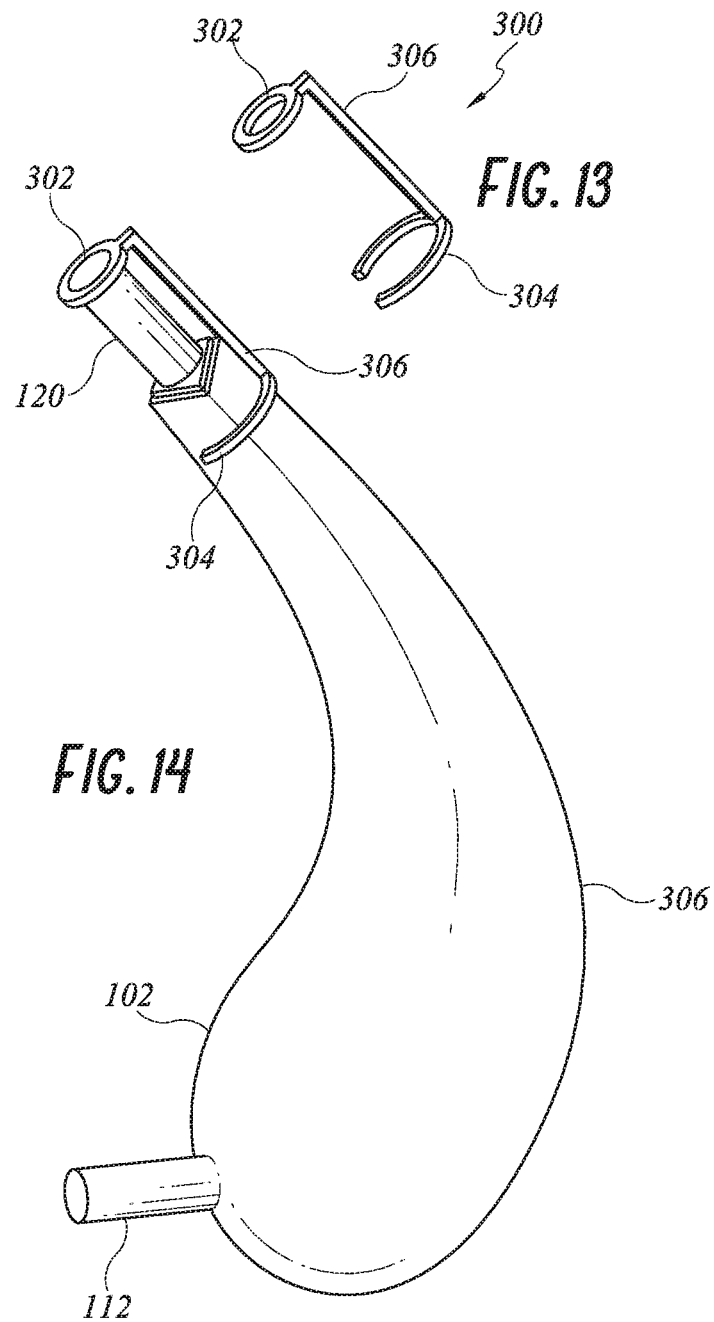

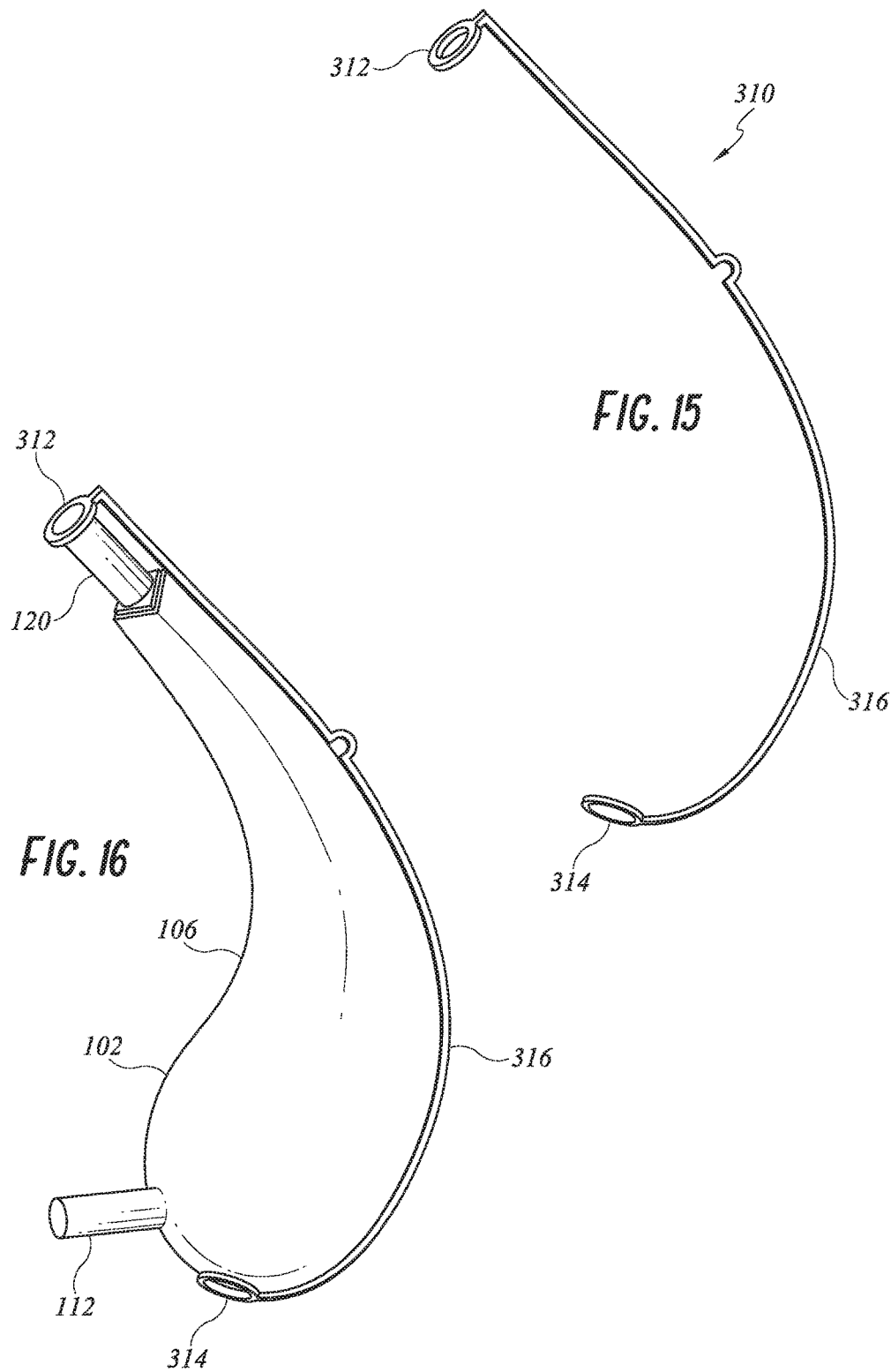

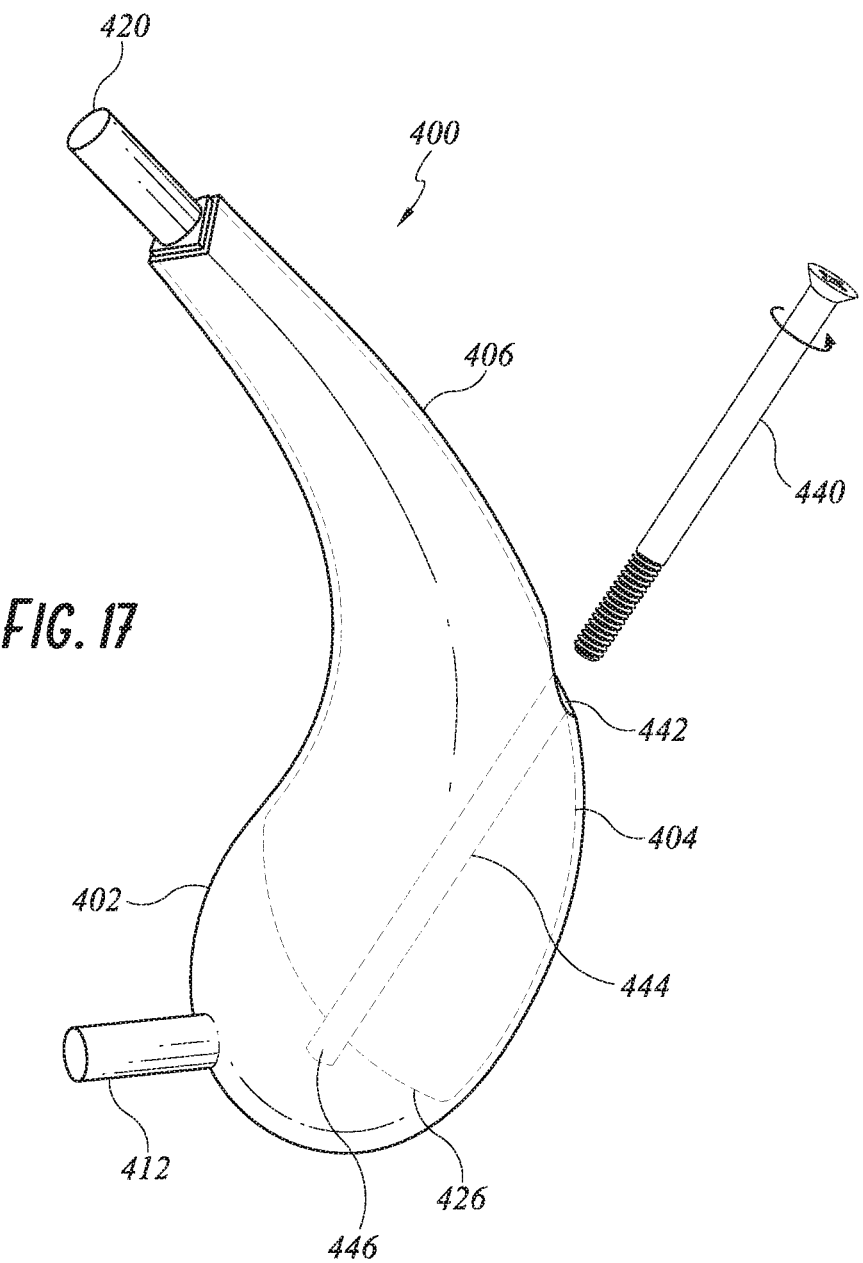

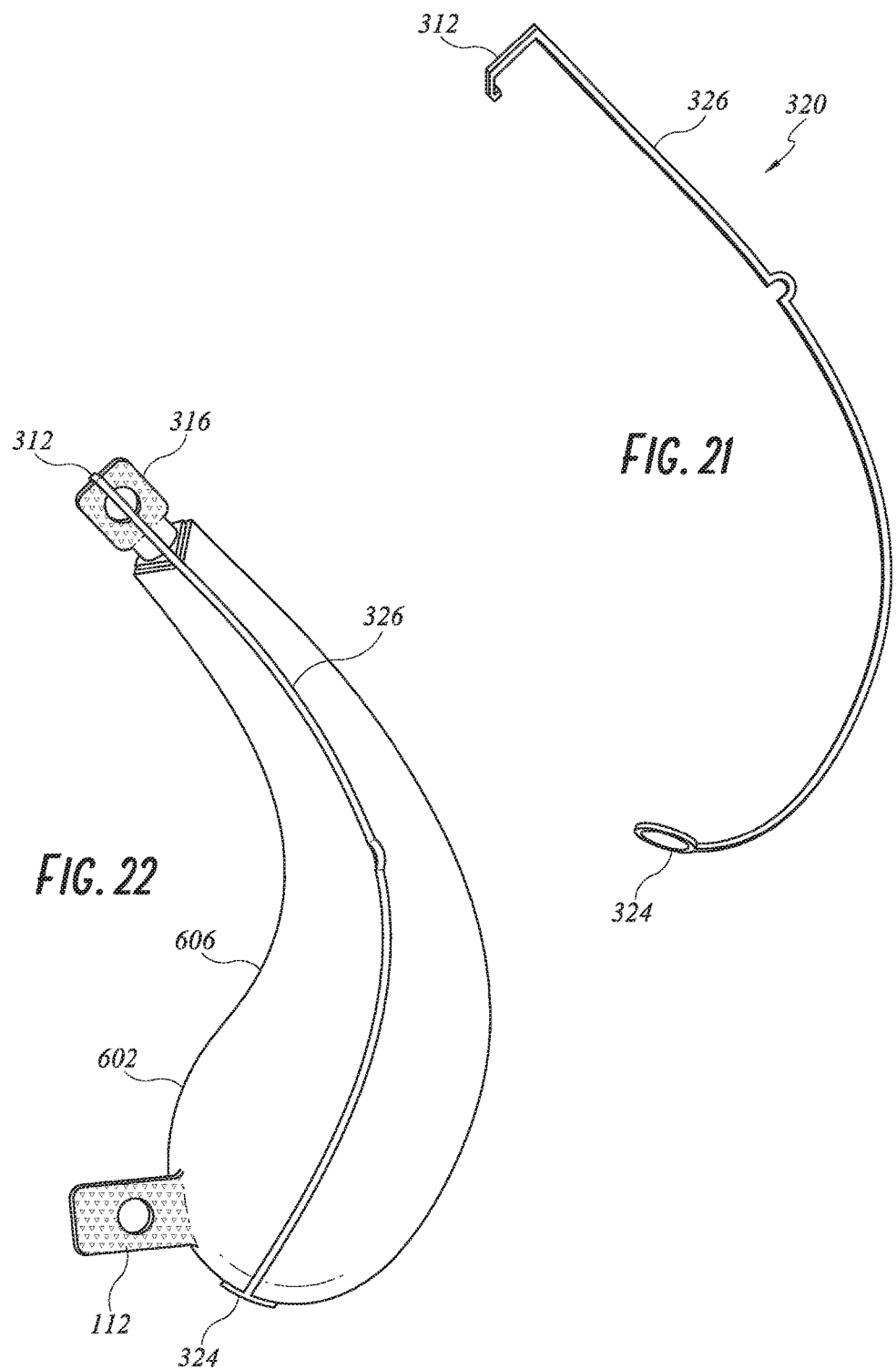

FACET JOINT REPLACEMENT DEVICE AND METHODS OF USE

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

The present application claims priority under 35 U.S.C. §119(e) to U.S. Provisional Patent Application Ser. No. 62/314,634, entitled "RESTORE UNILATERAL OR BILATERAL ARTIFICIAL LUMBAR FACET JOINT SURGICAL IMPLANT," filed Mar. 29, 2016, the entire disclosure of which is hereby expressly incorporated by reference.

BACKGROUND

Field

The present application relates to spinal surgery in general, and more particularly to methods, systems, and apparatuses for replacing a facet joint.

Description of the Related Art

The lumbar facet joint is a diarthrodial synovial joint consisting of a superior articular process having a superior articular surface, an inferior articular process having an inferior articular surface, and a capsule that encloses the superior and inferior articular surfaces. Each lumbar facet joint can provide mechanical support for axial loading along the spine, facilitate movement along a longitudinal axis of the spine, and limit relative rotation and translation of adjacent vertebra. Particularly, the articular processes support compressive loading and the capsule, resists forces developed across the facet joint due to movement of the adjacent vertebrae, such as, for example, rotational and translational forces. The facet joint capsule can provide resistance to separation of the superior and inferior articular surfaces and to relative motion between the superior and inferior articular surfaces.

Lumber facet joint dysfunction can develop as a result of degeneration, trauma, or neoplastic processes to the vertebrae and can result in spinal instability, malalignment, nerve compression, and pain, which can cause neurological deficits. Facet joint dysfunction is treated by partial or total resection of the dysfunctional lumbar facet joint. Resection can leave the addressed spinal motion segment with decreased strength, stiffness, and the ability to resist rotation.

Fusion procedures have evolved to address the spinal de-stabilization of motion segments caused by facet joint resection. Fusion procedures result in immobilization of the two adjacent vertebrae that comprise the motion segment. As physiologic loads are transmitted across contiguous motions segments of the lumbar spine, the introduction of an immobilized motion segment within the lumbar spine can result in non-physiologic transmission of these forces. This "disconnection" within the series of motion segments that comprise the lumbar spine has been postulated to create an altered force load application on the adjacent, non-treated, motion segments, potentially accelerating the degenerative process at these locations.

SUMMARY

Methods, systems and apparatuses are provided in certain embodiments of the present application to replace a dysfunctional facet joint.

In one embodiment, a facet joint replacement device is provided. The facet joint replacement device includes an enclosing element including an enclosing body and an inferior attachment member. The enclosing body includes a superior end having an opening, an inferior end, and an inner cavity defined by an interior surface of the enclosing body, wherein a portion of the interior surface of the enclosing body forms a superior articulating surface. The inferior attachment member extends from the enclosing body and is configured to attach to an inferior vertebral body. The facet joint replacement device also includes an inferior articulating element including an articulating body and a superior attachment member. The inferior articulating body is positioned within the inner cavity of the enclosing body of the enclosing element and is configured to move within the inner cavity of the enclosing body of the enclosing element. The inferior articulating body includes a superior end and an inferior end forming an inferior articulating surface. The superior attachment member extends from the superior end of the articulating body and superior to the opening of the superior end of the enclosing body. The superior attachment member is configured to attach to a superior vertebral body. The movement of the articulating body of the inferior articulating element is constrained in at least one direction within the inner cavity of the enclosing body of the enclosing element.

In another embodiment, a facet joint replacement system is provided. The facet joint replacement system includes the facet joint replacement device, an inferior fastener configured to secure the inferior attachment member to the inferior vertebral body, and a superior fastener configured to secure the superior attachment member to the superior vertebral body.

In another embodiment, a method of implanting a facet joint replacement device is provided. The method includes providing the facet joint replacement device, securing the superior attachment member to the superior vertebral body, and securing the inferior attachment member to the inferior vertebral body.

In another embodiment, a method of replacing a facet joint is provided. The method includes resecting at least a portion of a facet joint defined by an articular process of a superior vertebral body and an articular process of an inferior vertebral body, cannulating a pedicle of the inferior vertebral body and a pedicle of the superior vertebral body, inserting a first fastener into the pedicle of the inferior vertebral body and a second fastener into the pedicle of the superior vertebral body, and securing a facet joint replacement device to the first fastener and the second fastener, wherein the facet joint replacement device includes an enclosing body, an inferior articulating surface enclosed within the enclosing body, and a superior articulating surface enclosed within the enclosing body.

BRIEF DESCRIPTION OF THE DRAWINGS

FIG. 2A depicts a posterior perspective view of an enclosing element 102.

FIG. 2B depicts a posterior perspective view of an inferior articulating element 104.

FIG. 3A depicts an anterior perspective view of the enclosing element 102.

FIG. 3B depicts an anterior perspective view of the inferior articulating element 104.

FIG. 4 depicts a partial cross-sectional view of the enclosing element 102 showing a cross-section superior to a superior articulating surface 128.

FIG. 5 depicts a first sagittal view of the facet joint replacement device 100.

FIG. 6 depicts a second sagittal view of the facet joint replacement device 100.

FIG. 13 depicts a perspective view of a removable clip 300.

FIG. 14 depicts perspective view of the removable clip 300 secured to the facet joint replacement device 100.

FIG. 15 depicts a perspective view of a removable clip 310.

FIG. 16 depicts a perspective view of the removable clip 310 secured to the facet joint replacement device 100.

FIG. 17 depicts a posterior perspective view of a facet joint replacement device 400 and a fastener 440.

FIG. 21 depicts a perspective view of a removable clip 320.

FIG. 22 depicts a perspective view the removable clip 320 secured to the facet joint replacement device 600.

DETAILED DESCRIPTION

Figure 1A:
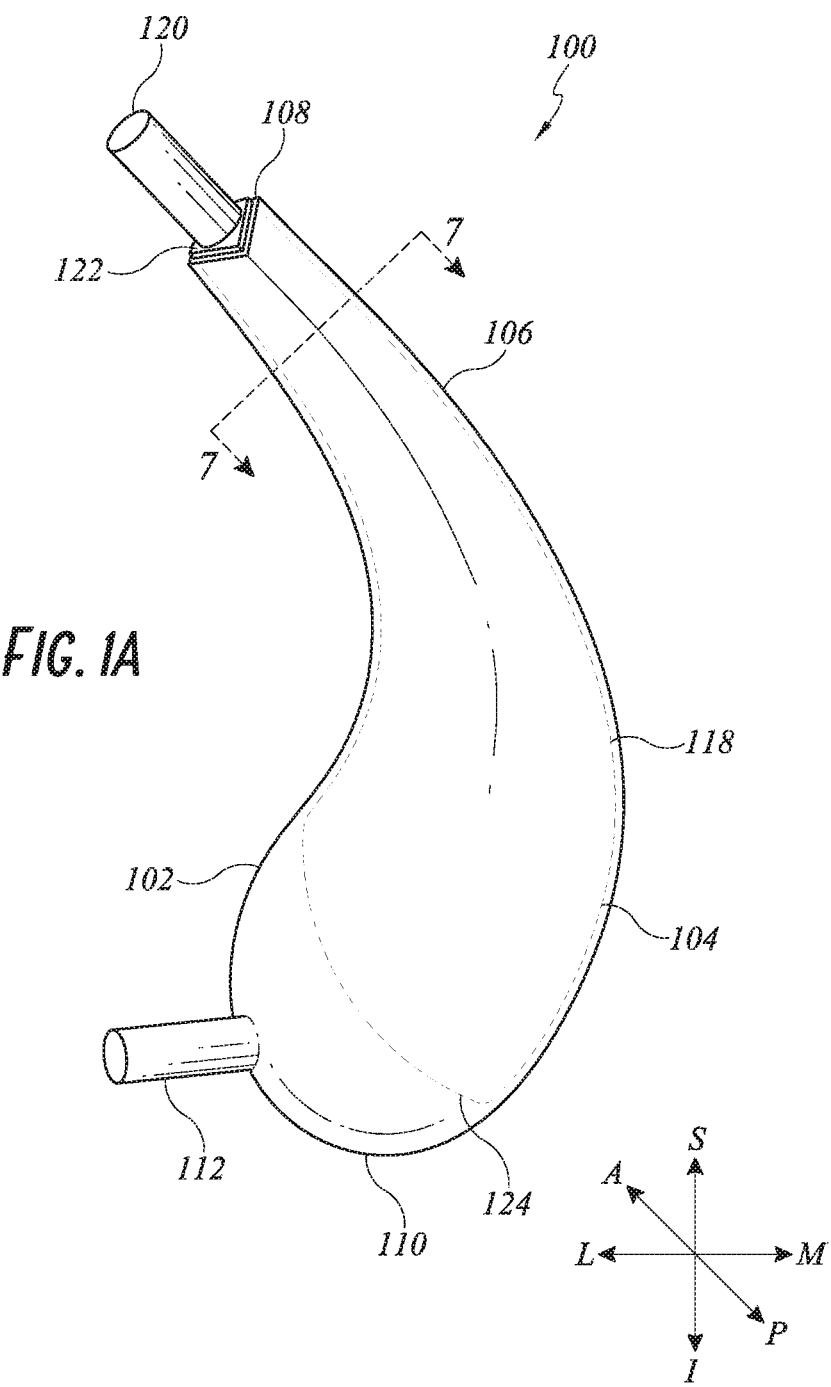
FIG. 1A depicts a posterior perspective view of the facet joint replacement device 100 showing interior components in dotted lines.

Methods, systems, and apparatuses are provided in certain embodiments of the present invention to replace a dysfunctional facet joint. In some embodiments a facet joint replacement device is provided. The facet joint replacement device can be configured to replace a facet joint that has been partially or fully resected. Following replacement, the facet joint replacement device can be configured to perform the function of a facet joint within a spinal motion segment. For example, the facet joint replacement device can include one or more components configured to perform the functions of a superior articular process, and inferior articular process, and/or a facet joint capsule. In some embodiments, the facet joint replacement device can include an enclosing element and one or more interior components positioned within an inner cavity of the enclosing element. The interior components can be configured to move within the enclosing element to facilitate movements of a spinal motion segment that simulate the movements allowed by a healthy facet joint in the human body. For example, the facet joint replacement device can allow for limited posterior/anterior motion, limited medial/lateral motion, and/or limited superior/inferior motion. The facet joint replacement device can also limit relative rotation and translation of adjacent vertebrae. For example, in some embodiments, the inner cavity of the enclosing element can be shaped and/or dimensioned to limit relative movement of the interior components within the enclosing element in at least one direction. In some embodiments, the enclosing element is shaped and/or dimensioned to limit relative movement in similar directions to a healthy facet joint capsule.

In some embodiments, the enclosing element can include a surface configured to simulate a superior articular surface of a healthy facet joint. In some embodiments, at least one of the internal components can include a surface configured to simulate an inferior articular surface that complements of a healthy facet joint. The enclosing body can be configured to provide resistance to or otherwise limit relative disassociation and/or rotation between the surfaces configured to simulate the superior articular surface and the inferior articular surface. The enclosing body can also maintain an intraarticular environment by encapsulating the surfaces configured to simulate the superior articular surface and the inferior articular surface. For example, the enclosing cylinder can act as a physical barrier to fibrosis at the surfaces configured to simulate the superior articular surface and the inferior articular surface. The enclosing cylinder can also act as a physical barrier to prevent friction wear to the adjacent anatomy due to relative movement between the surfaces configured to simulate the superior articular surface and the inferior articular surface In some embodiments, a body of the enclosing element can be shaped to conform to the shape of superior and inferior articular processes and a pars interarticularis of a healthy vertebral body. The shape of the enclosing element can be configured to support axial loading in a similar manner as healthy articular processes.

In some embodiments, at least some of the components of the facet joint replacement device can be designed such that assembly of the facet joint replacement device can be performed outside of the body. Such a facet joint replacement device can facilitate ease of implantation, as well as minimally invasive techniques.

FIGS. 1A-7 depict a facet joint replacement device 100 according to one embodiment. The terms superior, inferior, anterior, posterior, medial, and lateral, when describing portions of the devices herein, refer to portions of the device as they are intended to be oriented with respect to the human spine. FIG. 1A depicts a posterior perspective view of the facet joint replacement device 100 showing interior components in dotted lines. FIG. 1A also includes three-dimensional coordinate axes indicating the superior ("S"), inferior ("I"), anterior ("A"), posterior ("P"), medial ("M"), and lateral ("L") directions. As shown in the three-dimensional coordinate axes in FIG. 1A, the posterior direction P is generally pointing out of the page and the anterior direction A is generally pointing into the page. The facet joint replacement device 100 includes an enclosing element 102 and an inferior articulating element 104 positioned at least partially within the enclosing element 102. The articulating element 104 is referred to as an inferior articulating element because it provides a generally inferiorly facing articulating surface to engage a corresponding generally superiorly facing articulating surface on the enclosing element 102, as described further below.

The enclosing element 102 includes an enclosing body 106 and an inferior attachment member 112. The enclosing body 106 can have a generally arcuate shape configured to correspond to the shape of a pars interarticularis of a vertebra. The enclosing body 106 includes a superior end 108 and an inferior end 110. The inferior attachment member 112 extends laterally from the enclosing body 106 at a segment of the enclosing body adjacent to the inferior end 110. The enclosing body 106 further include an inner cavity 114 (shown in FIG. 4) defined by an interior surface of the enclosing body 106 and an opening 116 (shown in FIG. 2A) at the superior end 108. A portion of the interior surface of the enclosing body 106 can be shaped to form a superior articulating surface 128 (shown in FIG. 4). In some embodiments, the enclosing body 106 is configured to protect the surrounding anatomy from friction, damage, or infection due to the movement of components, including the inferior articulating surface 126 and superior articulating surface 128 in the interior of the enclosing body 106, for example, by acting as a physical barrier. For example, the enclosing body 106 can protect an adjacent thecal sac and adjacent nerve roots from involvement with the articulating surfaces 126 and 128 during relative movement between the articulating surfaces 126 and 128. In some embodiments, the enclosing body 106 is configured to protect the components within the interior of the enclosing body 106 from damage, wear, or fibrosis due to the surrounding anatomy, for example, by acting as a physical barrier.

The inferior articulating element 104 includes an articulating body 118 and a superior attachment member 120. The articulating body 118 is at least partially positioned within and configured to move within the inner cavity 114 of the enclosing body 106. The inferior articulating body 118 has a superior end 122 and an inferior end 124. The superior attachment member 120 extends superior to the superior end 122 of the articulating body 118. In some embodiments, the superior attachment member 120 extends through the opening 116. In some embodiments, a portion of the articulating body 118 extends superior to or in alignment with the opening 116. The inferior end 124 of the articulating body 118 forms an inferior articulating surface 126.

The superior attachment member 120 and inferior attachment member 112 can be shaped and/or dimensioned to facilitate securement of the facet joint replacement device 100 to the spine. As shown in FIG. 1A, the superior attachment member 120 and inferior attachment member 112 can each be a rod. However, the superior attachment member 120 and inferior attachment member 112 can be any shape suitable for fixation directly or indirectly to a vertebral body.

In some embodiments, the enclosing element 102 and/or the inferior articulating element 104 can consist of or consist partially of one or more metals or metal alloys. For example, the enclosing element 102 and/or articulating element 104 can consist of cobalt-chromium, titanium, titanium-based alloys, or any other suitable metals or metal alloys. In some embodiments, the enclosing element 102 and/or inferior element 104 can be ceramic or partially ceramic. In some embodiments, the enclosing element 102 and/or inferior element 104 can include super-hard ceramics.

Figure 1B:
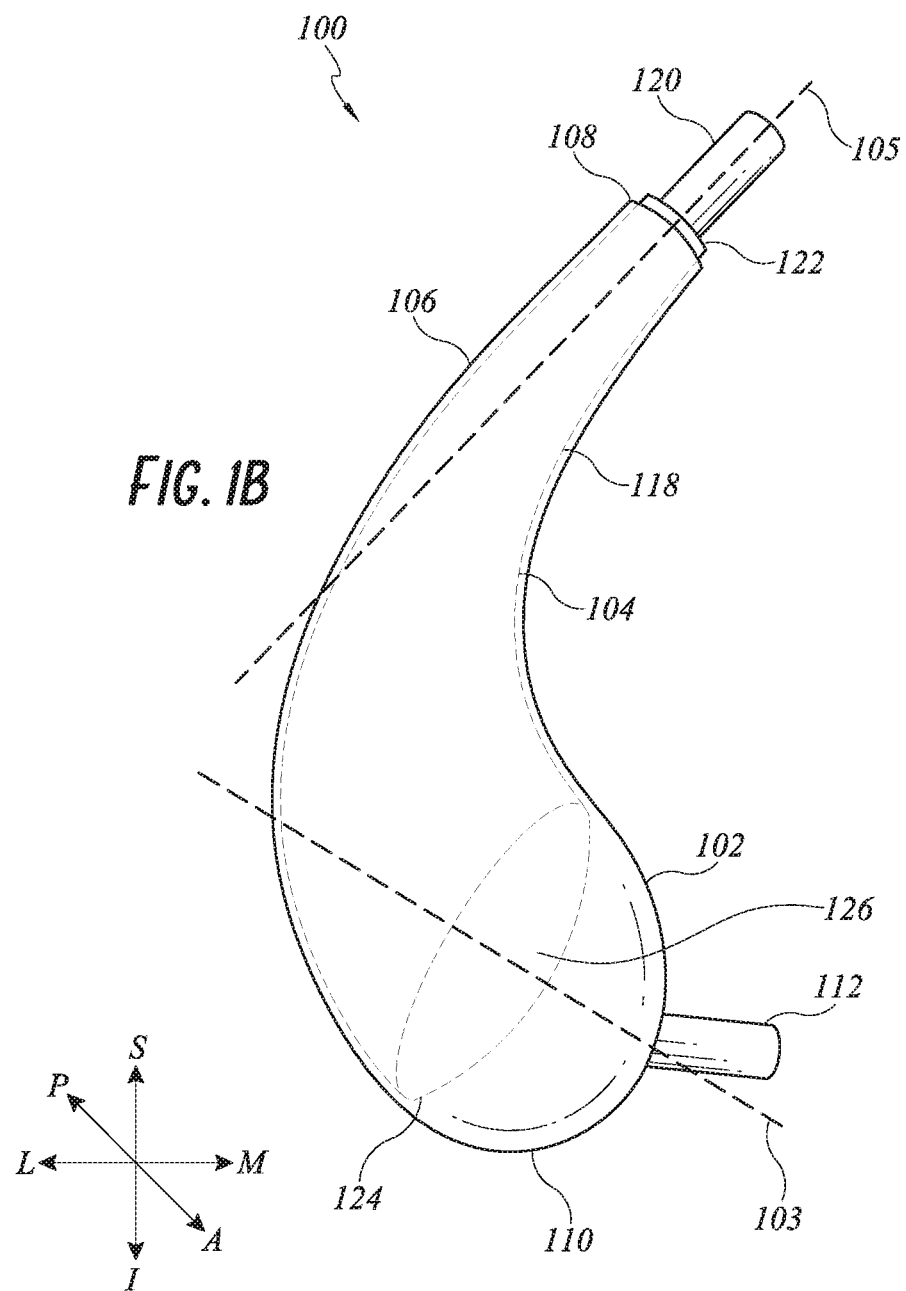
FIG. 1B depicts an anterior perspective view of the facet joint replacement device 100.

FIG. 1B depicts an anterior perspective view of the facet joint replacement device 100. FIG. 1B also includes three-dimensional coordinate axes indicating the superior ("S"), inferior ("I"), anterior ("A"), posterior ("P"), medial ("M"), and lateral ("L") directions. As shown in the three-dimensional coordinate axes of FIG. 1B, the anterior direction A is generally pointing out of the page and the posterior direction P is generally pointing into the page. As shown in FIG. 1B, the inferior articulating surface 124 can be configured to face at least partially in an anterior direction, as well as in a generally inferior direction and a generally lateral direction.

FIG. 1B also shows an axis 103 extending through a center point of the inferior articulating surface and an axis 105 extending through a long axis of the attachment member 120. Both the axis 105 and the axis 103 have superior-inferior, lateral-medial, and posterior-anterior components.

FIGS. 2A and 2B depicts a posterior perspective view of the enclosing element 102 and a posterior perspective view of the inferior articulating element 104, respectively. FIG. 2A shows the opening 116 through which a portion of the articulating body 118 can extend or align with when positioned within the enclosing body 106 of the enclosing element 102.

FIGS. 3A and 3B depict an anterior perspective view of the enclosing element 104 and an anterior perspective view of the inferior articulating element 104, respectively. As illustrated in FIG. 3B, the inferior articulating surface 126 can be ellipsoid or generally elliptical. The inferior articulating surface 126 can also be convex or at least partially convex. The inferior articulating surface 126 can be shaped and/or dimensioned to correspond to the shape, size, and/or convexity of an articular surface of a healthy inferior articular process.

FIG. 4 depicts a partial cross-sectional view of the enclosing element 102 showing a cross-section superior to the superior articulating surface 128. FIG. 4 shows the inner cavity 114 defined by the interior surface of the enclosing body 106 and the superior articulating surface 128. As illustrated in FIG. 4, the inner cavity 114 narrows between the superior articulating surface 128 and the superior end 108 of the enclosing body 106. As illustrated in FIG. 4, superior articulating surface 128 can be defined by a section of the interior surface of the enclosing body 106. The superior articulating surface 128 can be ellipsoid or generally elliptical. The superior articulating surface 128 can also be concave or at least partially concave. The superior articulating surface 128 can be shaped/and or dimensioned to correspond to the shape, size, and/or concavity of an articular surface of a healthy superior articular process.

While the inferior articulating surface 126 and superior articulating surface 128 are shown as elliptical in FIGS. 3B and 4, any suitable complementary surface shapes can be used. In some embodiments, the inferior articulating surface 126 and superior articulating surface 128 are circular or generally circular, oval or generally oval, rounded, polygonal, oblong, symmetric, asymmetric, or any other suitable shape. In some embodiments, the inferior articulating surface 126 and superior articulating surface 128 can be shaped such that force is applied symmetrically to the superior articulating 128 when the inferior articulating element 126 contacts or otherwise applies a force upon the superior articulating surface 126.

As described further herein, the articulating body 118 is configured to move within the enclosing body 106 in at least one direction. When the superior attachment member 120 is secured to a superior vertebral body and the inferior attachment member 112 is secured to an inferior vertebral body, movement between the superior and inferior vertebral bodies can cause movement of the superior attachment member 120 with respect to the position of the enclosing body 106 resulting from the inferior attachment member 112 being secured to the inferior vertebral body. Movement of the superior attachment member 120 with respect to the enclosing body 106 causes movement of the articulating body 118 within the enclosing body 106 generally along the inner wall of the enclosing body. Referring again to FIG. 1B, the superior attachment member 120 is configured to move along axis 105 towards and away from the enclosing body 106. When the superior attachment member 120 moves towards the enclosing body 106 along the axis 105, the superior attachment member 120 moves along the axis 105 in a medial, anterior, and inferior direction. When the superior attachment member 120 moves away from the enclosing body 106 along the axis 105, the superior attachment member 120 moves along the axis 105 in a lateral, posterior, and superior direction. The superior end 122 of the articulating body 118 moves along the axis 105 in the same manner when the superior attachment member 120 moves along the axis 105. Although relative movement of the superior attachment member 120 towards and away from the enclosing body 106 is discussed, one of skill in the art would understand that movement between the enclosing body 106 and superior attachment member 120 could be described as movement of the enclosing body 106 towards or away from the superior attachment member 120 or movement of the enclosing body 106 and superior attachment member 120 towards or away from each other.

Movement of the superior attachment member 120 with respect to the enclosing body 106 causes movement of the inferior articulating surface 126 along the axis 103 towards and away from the superior articulating surface 128. The inferior articulating surface 126 moves towards the superior articulating surface 128 along the axis 103 when the superior attachment member 120 moves towards the enclosing body 106, and the inferior articulating surface 126 moves away from the superior articulating surface 128 when the superior attachment member 120 moves away from the enclosing body 106. When the inferior articulating surface 126 moves away from the superior articulating surface 128 along the axis 103, the inferior articulating surface moves along the axis 103 in a superior, posterior, and medial direction. When the inferior articulating surface 126 moves towards the superior articulating surface 128 along the axis 103, the inferior articulating surface moves along the axis 103 in an inferior, anterior, and lateral direction. Although relative movement of the inferior articulating surface 126 towards and away from the superior articulating surface 128 is discussed, one of skill in the art would understand that movement between the inferior articulating surface 126 and the superior articulating surface 128 could be described as movement of the superior articulating surface 128 towards or away from the inferior articulating surface 126 or movement of the inferior articulating surface 126 and the superior articulating surface 128 towards or away from each other. In some embodiments, the axis 103 extends through a center point of the superior articulating surface 128. In some embodiments, the axis 103 extends transverse to a tangent of a center line of the inferior articulating surface 126. The axis 103 can represent the direction of relative movement between the articular surfaces of a healthy facet joint.

In some embodiments, the enclosing body 106 acts to limit relative movement between the inferior articulating surface 126 and the superior articulating surface 128 along the axis 103. In some embodiments, the enclosing body 106 acts to limit relative movement of the inferior articling surface 126 and superior articulating surface 128 perpendicular to the axis 103.

When the articulating body 118 moves within the enclosing body 106, the inferior articulating surface 126 can contact the superior articulating surface 128. In some embodiments, the enclosing body 106 and inferior articulating body 118 are configured such that a maximum distance between a center point of the inferior articulating surface 126 and the superior articulating surface 128 is 0.5 mm, 1.0 mm, 1.5 mm, 1.75 mm, 2.0 mm, 2.25 mm, 2.5 mm, 3.0 mm, 3.5 mm, 4.0 mm, 5.0 mm, less than 2.0 mm, less than 3.0 mm, less than 4.0 mm, between 1.0 mm and 3.0 mm, between 1.0 mm and 2.0 mm, between 2.0 mm and 3.0 mm, between 1.5 mm and 2.5 mm, or between 1.75 mm and 2.25 mm. In some embodiments, the superior articulating surface 128 is shaped and/or dimensioned to receive the inferior articulating surface 126. As shown in FIG. 4, the enclosing body 106 includes a solid portion 130 between the superior articulating surface 128 and the inferior attachment member 112. In some embodiments, the solid portion 130 of the enclosing body 106 can have a depth dimensioned for receiving an axial load supplied by the articulating body 118 to the inferior articulating surface 126 due to movement of the articulating body 118 within the enclosing body 106.

Figure 7:
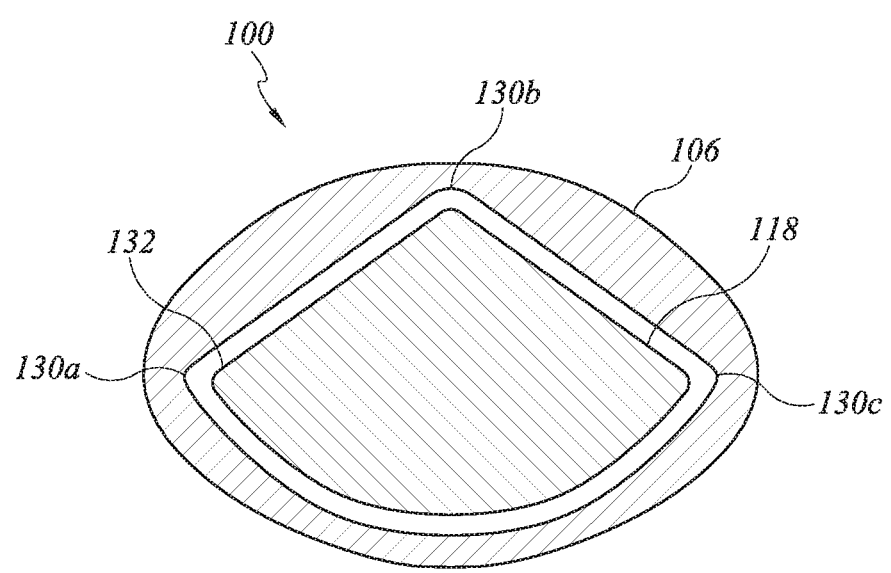
FIG. 7 depicts a cross-sectional view of the facet joint replacement device 100.

FIGS. 5 and 6 show a first sagittal view showing a lateral side of the facet joint replacement device 100 and a second sagittal view showing a medial side of the facet joint replacement device 100, respectively. FIG. 7 shows a cross-sectional view of the facet joint replacement device 100 taken along line 7-7 as show in FIG. 1A. As shown in FIG. 7, the interior surface of the enclosing body 106 includes a plurality of internal corners or grooves 130a, 130b, and 130b, each forming angle that corresponds to one of a plurality of external corners or edges 132 of the articulating body 118. Groove 130b is generally positioned within the posterior side of the facet joint replacement device 100. A linear portion extends between groove 130a and groove 130b. A second linear section extends between groove 130c and groove 130b. An arcuate section extends between groove 130a and groove 130c. The arcuate section between groove 130a and groove 130c is generally positioned within the anterior side of the facet joint replacement device 100. The grooves 130 can extend along one or more portions of the interior surface of the enclosing body 106. In some embodiments, the grooves 130 extend along a length of the interior surface of the enclosing body 106 from the superior end 108 to the superior articulating surface 128. The edges 132 can extend along one or more portions of the outer surface of the articulating body 118. In some embodiments, the edges 132 can extend along a length of the outer surface of the articulating body 118 between the superior end 122 to the inferior articulating surface 126. The grooves 130 of the enclosing body 106 can be configured to engage the edges 132 of the articulating body 118 to prevent relative rotation of the articulating body 118 within the enclosing body 106. The enclosing body 106 and articulating body 118 can be shaped and dimensioned to allow for relative axial movement between the inferior articulating surface 126 and the superior articulating surface 128 along the axis 103.

While three grooves 130 and three edges 132 are shown in FIG. 7, any number of grooves and edges may be utilized to prevent relative rotation of the articulating body 118 within the enclosing body 106. One of skill in the art would recognize that the cross-sections of the inner wall of the enclosing body 106 and the outer surface of the articulating body 118 could be any corresponding non-circular cross-sections suitable to prevent relative rotation and allow for relative translation along the length of the enclosing body 106. For example, in some embodiments, the inner wall of the enclosing body 106 and the outer surface of the articulating body 118 can each have an oval cross-section.

As described herein, the components of the facet joint replacement device 100 can be shaped and/or dimensioned to correspond to the anatomy of a healthy facet joint and related spinal motion segment. While lumbar facet joints are shown and described herein, applications of the facet joint replacement device 100 are not limited to the lumbar spine. In some embodiments, the facet joint replacement device 100 can be shaped and/or dimensioned to correspond to the anatomy of the thoracic spine. In some embodiments, a vertical distance between the superior end 108 of the enclosing body and the inferior end 110 of the enclosing body is between 20 mm to 44 mm, between 24 mm to 40 mm, between 28 mm and 36 mm, or between 30 mm and 34 mm. In some embodiments a vertical distance between the superior end 108 of the enclosing body and the inferior end 110 of the enclosing body is 28 mm, 29 mm, 30 mm, 31 mm, 32 mm, 33 mm, 34 mm, 35 mm, or 36 mm.

In some embodiments, one or both of the superior articular surface 128 and inferior articular surface 126 can have a major axis length of 10 mm, 11 mm, 12 mm, 13 mm, 14 mm, 15 mm, 16 mm, 17 mm, 18 mm, between 10 mm to 25 mm, between 9 to 14 mm, between 10 to 14 mm, or between 12 mm to 14 mm. In some embodiments, one or both of the superior articular surface 128 and inferior articular surface 126 can have a minor axis length of 8 mm, 9 mm, 10 mm, 11 mm, 12 mm, 13 mm, 14 mm, 15 mm, 16 mm, 17 mm, 18 mm, between 8 mm to 25 mm, between 8 mm to 14 mm, between 9 mm to 14 mm, or between 12 mm to 14 mm.

In some embodiments, the superior articulating surface 128 can be oriented at an angle of between 75° to 95° or between 55° to 85° from a transverse anatomic plane. In some embodiments, the superior articulating surface 128 can be oriented at an angle of between −100° to −150° or between −65° to −85° from a sagittal anatomic plane. In some embodiments, the inferior articulating surface 128 can be oriented at an angle of between 60° to 90° or between 55° to 85° from a transverse anatomic plane. In some embodiments, the superior articulating surface 128 can be oriented at an angle of between −65° to −165° or between −65° to −145° from a sagittal anatomic plane.

In some embodiments, an angle between the axis 103 and axis 105 can be 60°, 70°, 80°, 90°, 100°, 110°, 120°, 130°, between 60° and 130°, between 70° and 120°, between 80° and 110°, between 90° and 100°, between 60° and 80°, between 80° and 100°, or between 100°, and 120°.

In some embodiments, an angle between a plane extending through the center point of the inferior articulating surface 126 and a plane defined by the superior end 122 of the articulating body 118 can be 60°, 70°, 80°, 90°, 100°, 110°, 120°, 130°, between 60° and 130°, between 70° and 120°, between 80° and 110°, between 90° and 100°, between 60° and 80°, between 80° and 100°, or between 100°, and 120°.

In some embodiments, one or both of the superior attachment member 120 and the inferior attachment member 112 can have a diameter of 1 mm, 2 mm, 3 mm, 4 mm, 4.5 mm, 5 mm, 5.5 mm, 6 mm, 6.5 mm, 7 mm, 8 mm, 9 mm, 10 mm, between 2 mm to 8 mm, between 4 mm to 6 mm, between 5 mm to 7 mm, or between 5 mm to 6 mm. In some embodiments, one or both of the superior attachment member 120 and the inferior attachment member 112 can have a length of 1 mm, 2 mm, 3 mm, 4 mm, 5 mm, 6 mm, 7 mm, 8 mm, 9 mm, 10 mm, 15 mm, 20 mm, 25 mm, 30 mm, between 2 mm to 8 mm, between 4 mm to 6 mm, between 5 mm to 10 mm, between 10 mm to 15 mm, between 15 mm to 20 mm, between 20 mm to 25 mm, between 25 mm to 30 mm, between 15 mm to 30 mm, or less than 15 mm.

In some embodiments, a thickness of the solid portion 130 between the superior articulating surface 128 and an inferior most point of the enclosing body 106 along the axis 103 can be 6 mm, 7 mm, 8 mm, 9 mm, 10 mm, 11 mm, 12 mm, 13 mm, 14 mm between 8 mm to 25 mm, between 6 mm to 14 mm, or between 8 mm to 12 mm.

In some embodiments, the widest section of the enclosing body 106 is at the superior articulating surface 128. The enclosing body 106 can include an inflection point at the superior articulating surface 128. In some embodiments, the enclosing body 106 bows medially between the superior articulating surface 128 and the superior end 108 of the enclosing body 106. In some embodiments, the articulating body 118 bows medially between the inferior articulating surface 128 and the superior end 122 of the articulating body 118.

Figure 8:
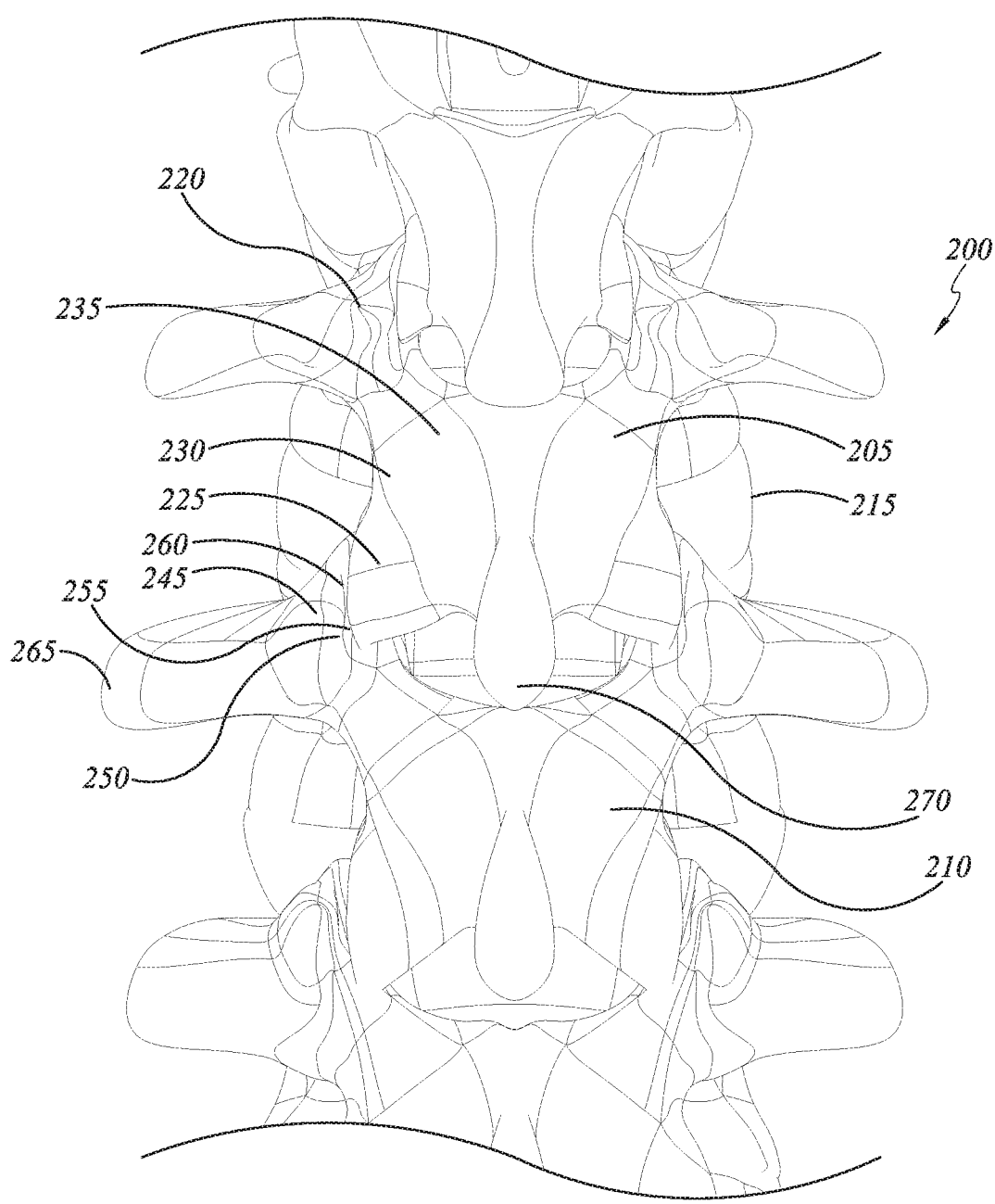
FIG. 8 depicts a posterior view of a lumbar motion segment 200.
Figure 9:
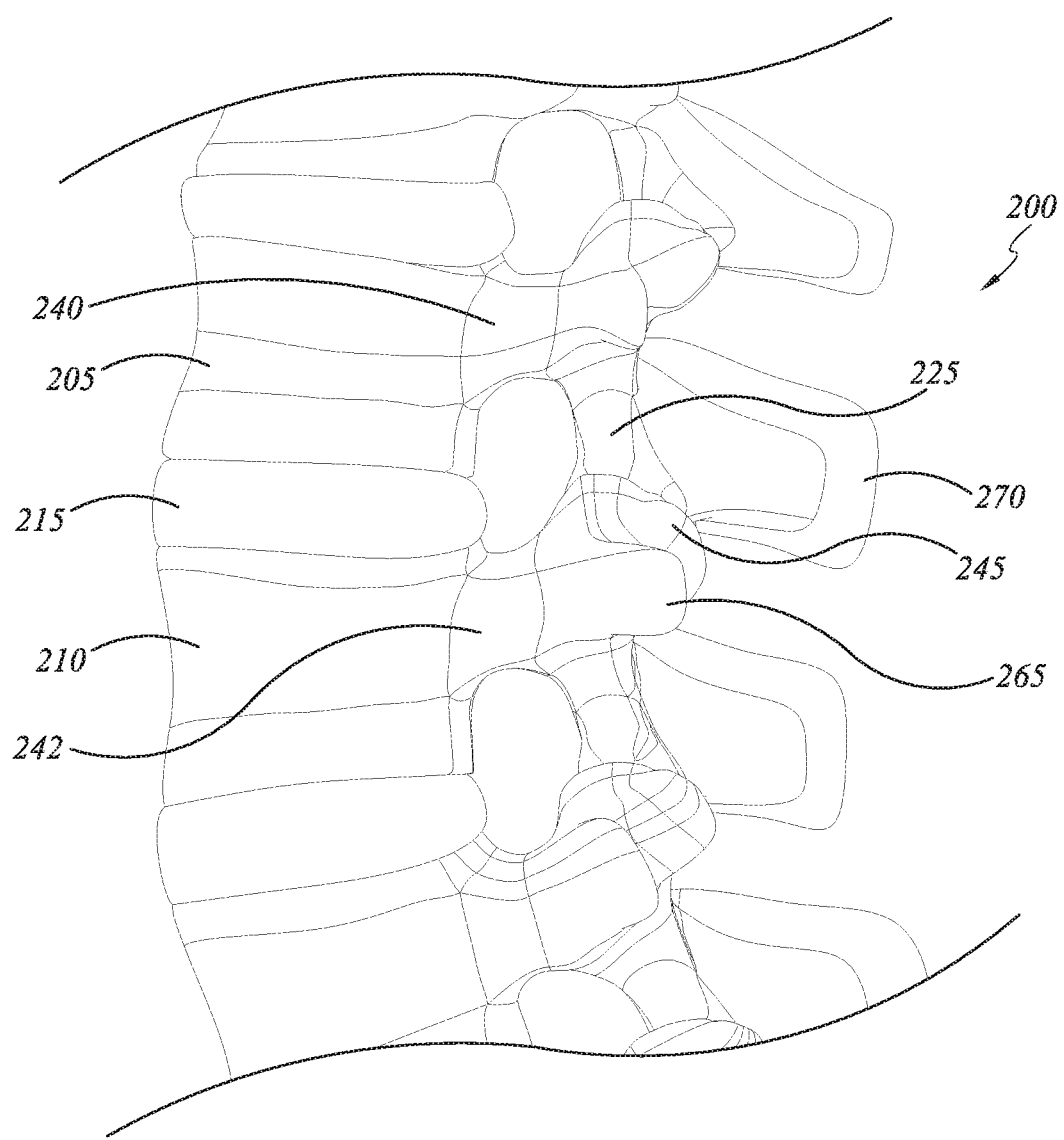
FIG. 9 depicts a sagittal view of the lumbar motion segment 200.

FIGS. 8 and 9 depict a posterior view and a sagittal view, respectively, of a lumbar motion segment 200 including a superior vertebra 205, an inferior vertebra 210, and an intervening disc 215. The superior vertebra 205 includes a superior articular process 220, an inferior articular process 225, and a pars interarticularis 230 extending between the superior articular process 220 and the inferior articular process 225. The pars interarticularis 230 is positioned between lamina 235 and pedicle 240. The pedicle 242 is also shown. A superior articular process 245 of the inferior vertebra 210 is also shown. An articular surface 250 of the superior articular process 245 and an articular surface 255 of the inferior articular process 225 align to form facet joint 260, which is encapsulated by a facet joint capsule (not shown). A sagittal inclination angle of the lumbar facet joint can range between 82° to 86°. As shown in FIG. 8, the facet joint 260 is located medial to transverse process 265 and lateral to spinous process 270. The facet joint is axially offset from the midline of the spine by between 15° to 70° degrees, dependent on the lumbar level, with more inferior lumbar segments have greater axial offset angles.

Figure 10:
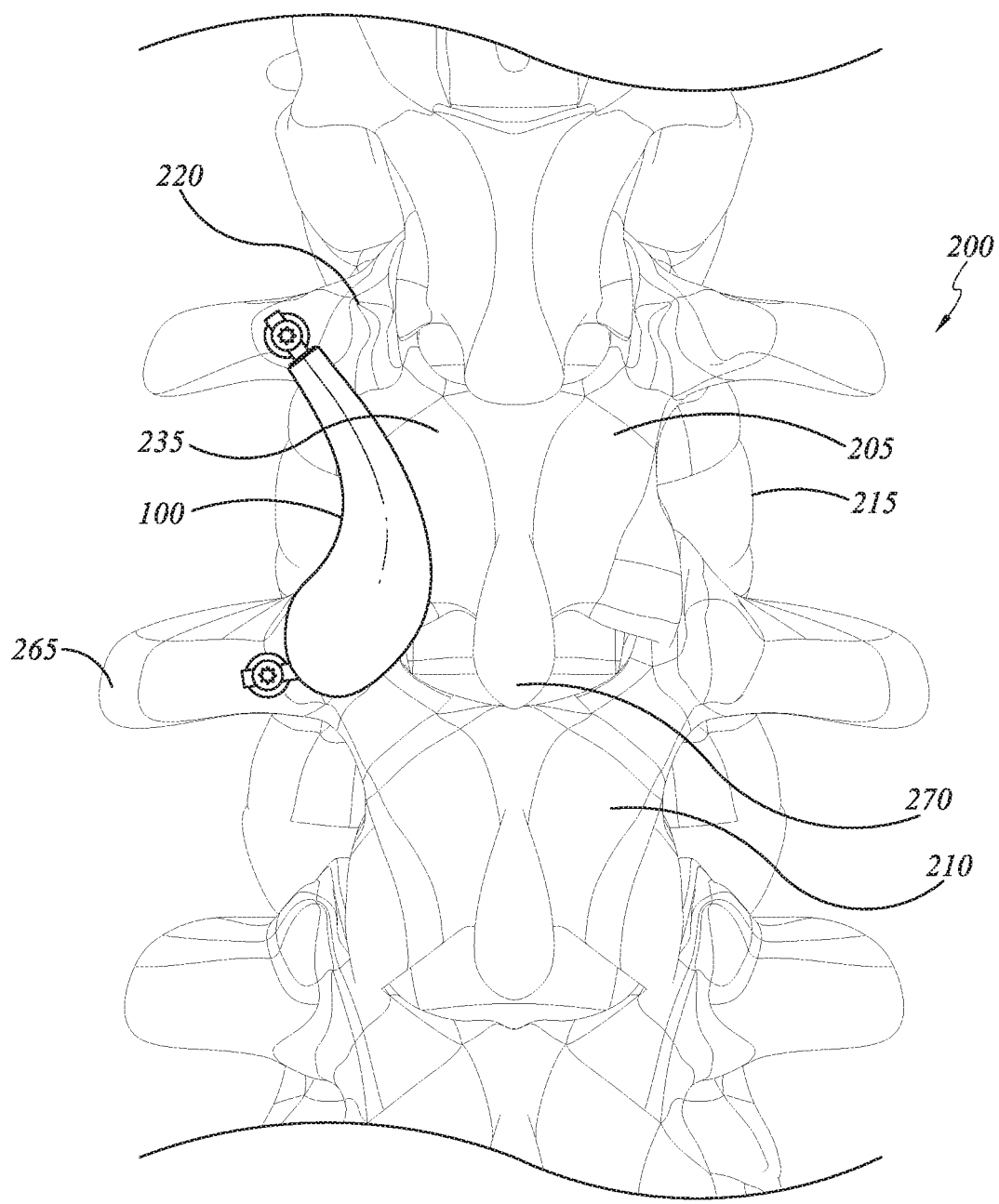
FIG. 10 depicts a posterior view of the lumbar motion segment 200 with the facet joint replacement device 100 implanted.
Figure 11A:
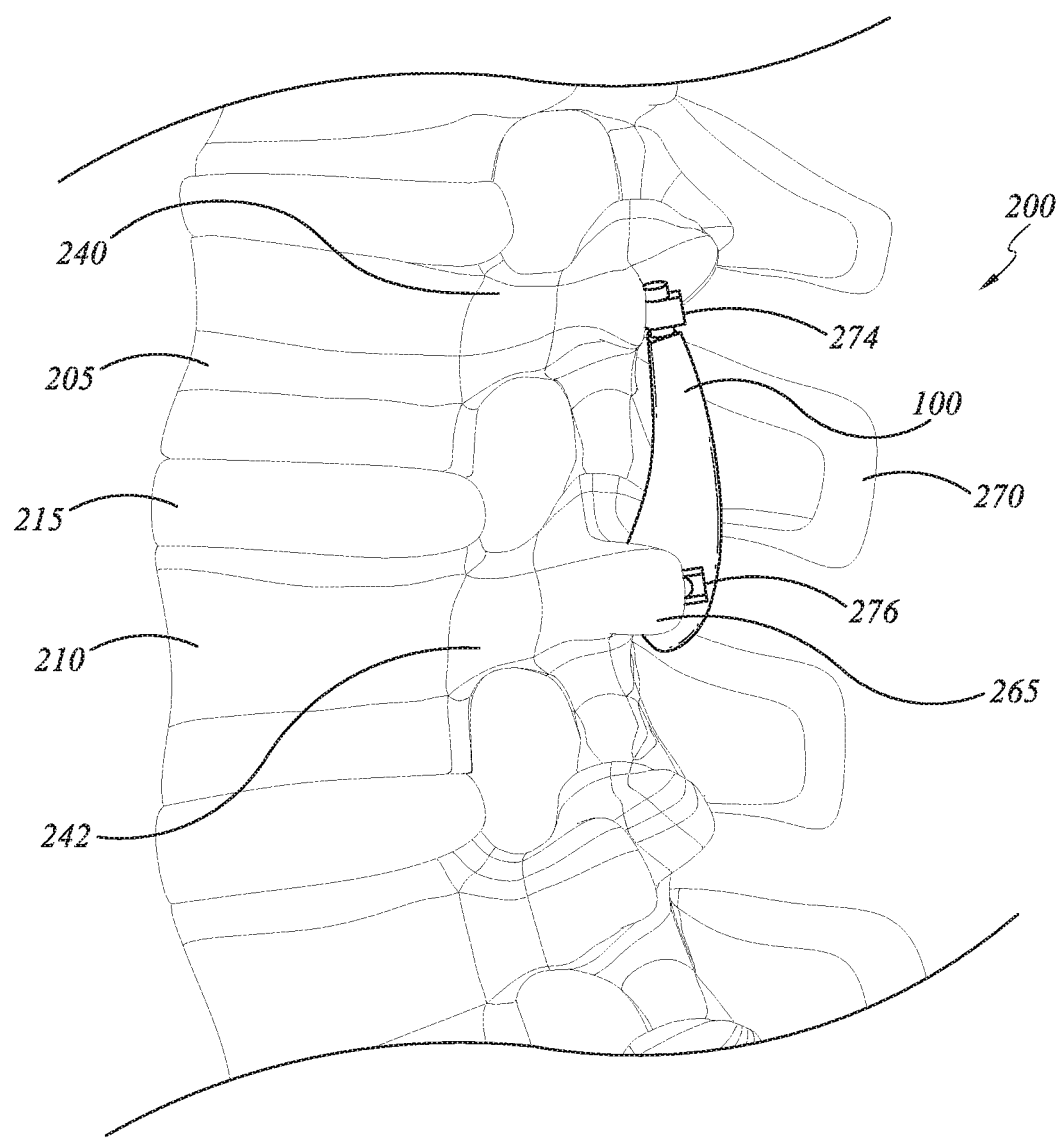
FIG. 11A depicts a sagittal view of the lumbar motion segment 200 with the facet joint replacement device 100 implanted.
Figure 11B:
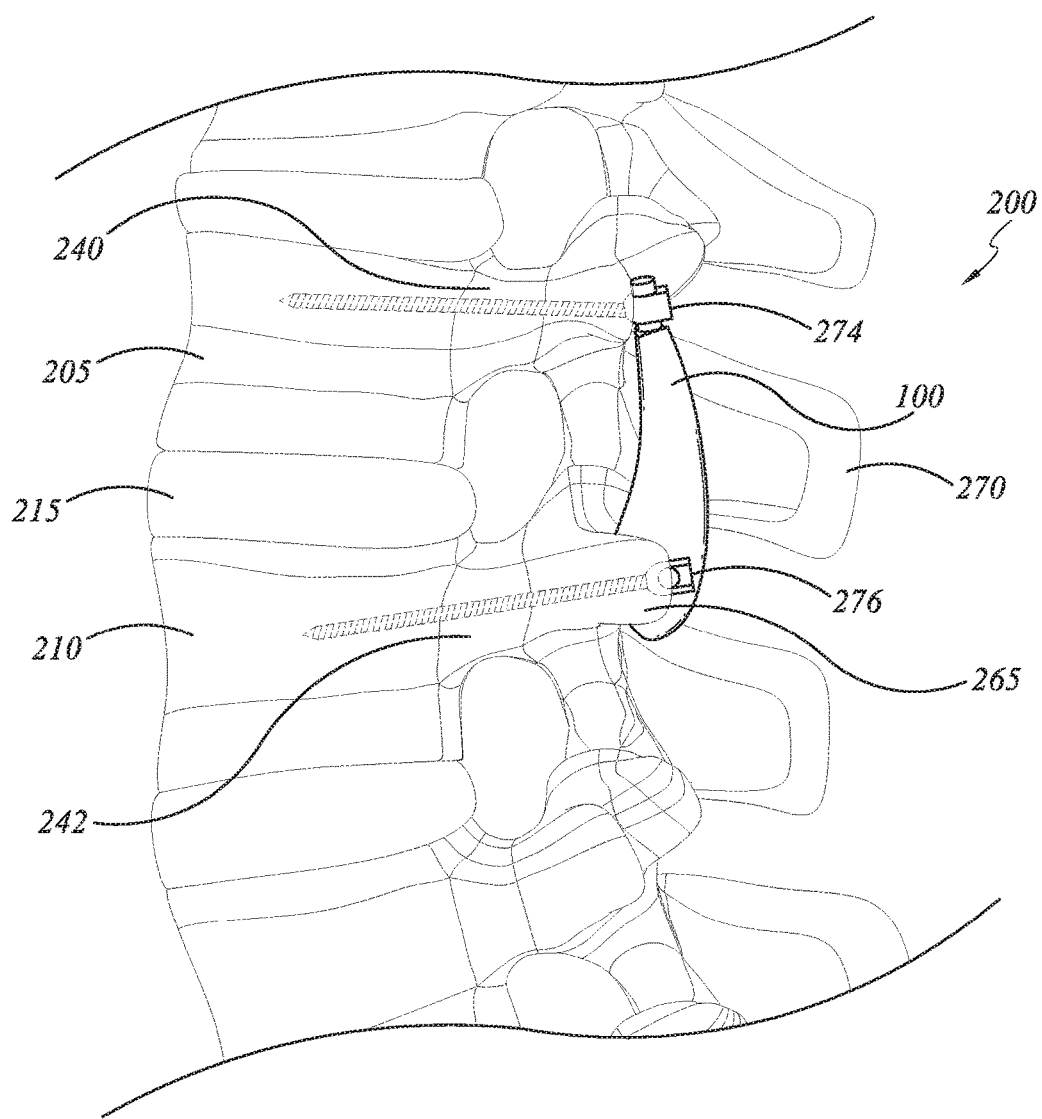
FIG. 11B depicts a sagittal view of the lumbar motion segment 200 with the facet joint replacement device 100 implanted showing components positioned within or obstructed by bone in dotted lines.

FIGS. 10 and 11A depict a posterior view and a sagittal view, respectively, of a lumbar motion segment 200 with the facet joint replacement device 100 implanted. The superior attachment member 120 is affixed to the pedicle 240 of a superior vertebra or superior vertebral body 205 by a fastener 274. The inferior attachment member 112 is affixed to the pedicle 242 of an interior vertebra or inferior vertebral body 210 by a fastener 276. As shown in FIGS. 10 and 11A, the fasteners 274 and 276 each include a tulip head bone screw and a top loading set screw. FIG. 11B shows the positioning of the tulip head bone screws of fasteners 274 and 276 within pedicles 240 and 242 in dotted lines.

Figure 12:
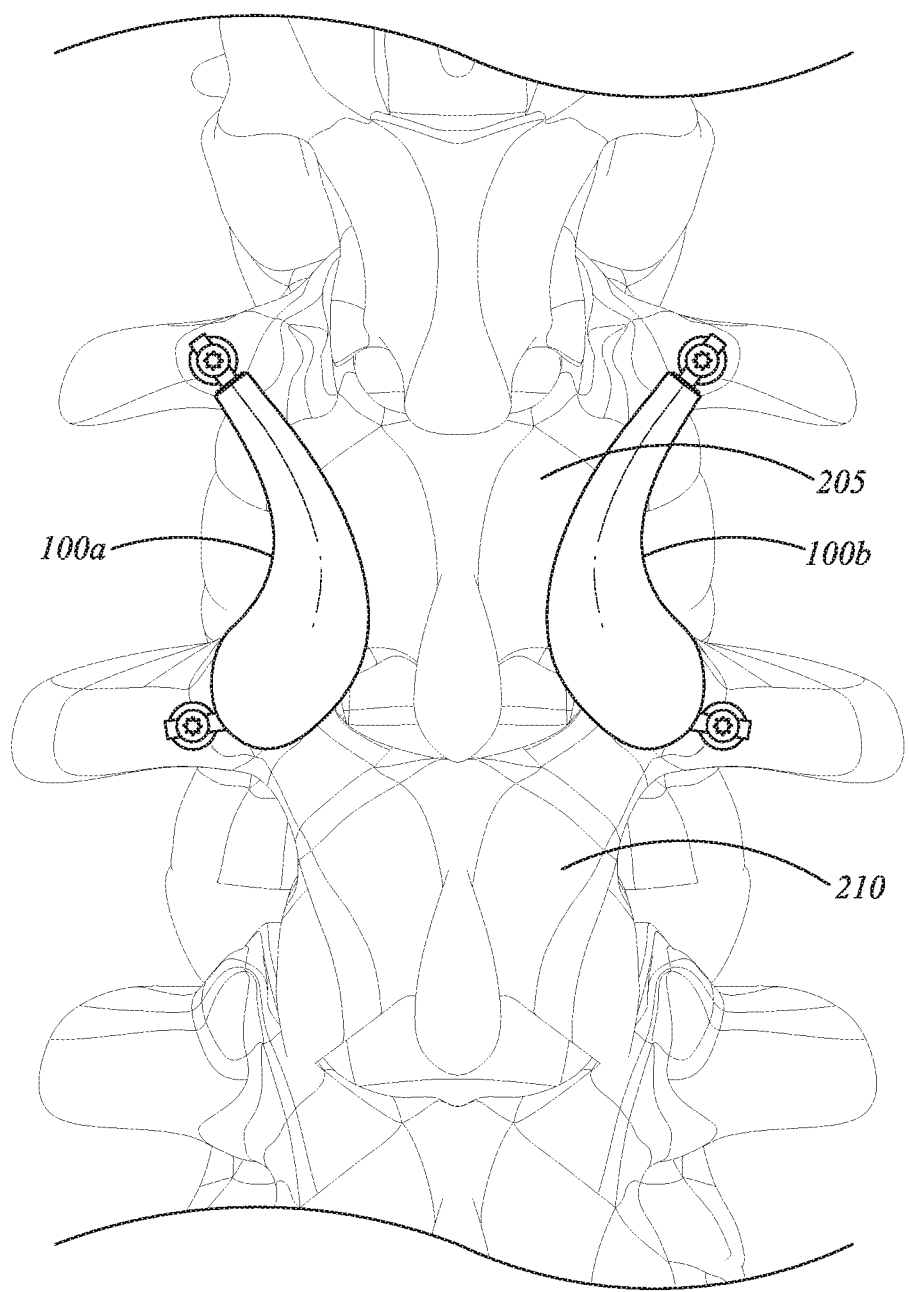
FIG. 12 depicts a posterior view of the lumbar motion segment 200 having a first facet joint replacement device 100A and a second facet joint replacement device 100B implanted bilaterally.

FIGS. 10 and 11A show a unilateral implantation of a facet joint replacement device 100. One of skill in the art would understand that a facet joint replacement device, such as facet joint replacement device 100, can be implanted on either lateral side of a motion segment, or two facet joint replacement devices can be implanted bilaterally, one on each side of a particular motion segment. FIG. 12 depicts a posterior view of the lumbar motion segment 200 having a first facet joint replacement device 100A positioned on a first lateral side of the lumbar motion segment 200 and a second facet joint replacement device 100B positioned on a second lateral side of the lumber motion segment 200.

In some embodiments, a method for implanting facet joint replacement device 100 into a patient begins with the administration of general endotracheal anesthesia. Following the administration of anesthesia, the patient is placed into a prone position and intraoperative fluoroscopy is used to identify a desired location for making a skin incision for implanting the facet joint replacement device 100. After the desired location is selected, a midline lumbar-sacral incision is made at the desired location, and subperiosteal dissection is utilized to expose a desired lamina, facet joint, and entry points to cannulate the ipsilateral pedicles of the superior and inferior vertebral bodies associated with the facet joint to be replaced. In some alternative embodiments, minimally invasive surgical techniques can be employed for exposure of the desired lamina, facet joint, and entry points to cannulate the ipsilateral pedicles. After exposure of the desired structures, intraoperative fluoroscopy is utilized to confirm desired levels of exposure. After the desired levels of exposure are confirmed, a self-retaining retractor system is placed to maintain the desired level of exposure.

After the retractor system is in place, removal of one or more sections of the facet joint and surrounding bone is performed. In some embodiments, the lamina or portion of the lamina in the motion region to be treated is removed. Removal can be performed using bone biters, angled curets, and/or bone punches. In some embodiments, a ligamentum flavum or a portion of the ligamentum flavum in the motion segment to be treated is removed. Removal of the ligamentum flavum can be performed using bone punches. The facet joint or a portion of the facet joint to be treated is also removed. Removal of the facet joint can be performed using a high speed drill, bone biters, and/or bone punches. After removal of the facet joint to be treated, further decompression of the lateral recess can be performed and adjacent nerve roots can be identified. Additional bone may be removed as necessary to prevent mechanical compression of the nerve roots.

Following removal of the desired bone, the pedicles of the superior vertebral body and inferior vertebral body of the motion segment to be treated and desired points of entry to cannulate the pedicles are identified, for example, using intraoperative fluoroscopy. A high speed drill or bone awl is then used to perforate the cortical bone overlying the optimal entry points to cannulate each of the pedicles. The pedicles are then probed and tapped under fluoroscopic guidance. Tulip head bone screws, such as the tulip head bone screws of fasteners 274 and 276, are then screwed into the previously tapped pedicles. Additional fixation augmentors, such as methylmethacrylate, can also be used. In some embodiments, a decision to use additional fixation augmentors is made based on apparent bone quality at the time of bone screw insertion. Methylmethacrylate or other fixation augmentors can be placed within the cannulated pedicle prior to placement of the bone screw, for example, to improve the fixation of the bone screw within the implanted pedicle bone.

After fixation of the bone screws to the superior and inferior vertebral bodies, the superior attachment member 120 can be placed within a receiving portion of the tulip head portion of the bone screw in the superior vertebral body, and the inferior attachment member 112 can be placed within a receiving portion of the tulip head portion of the bone screw in the inferior vertebral body. After the superior attachment member 120 and inferior attachment member 112 are received within the tulip head portions of the implanted bone screws, the superior attachment member 120 and inferior attachment member 112 can be secured to the bone screws by fixation of top loading set screws to each of the tulip head portions of the implanted bone screws.

In some embodiments, after ensuring that the implanted bone screws are in proper position and secure, but before the attachment members 120 and 112 are placed into the bone screws, distraction or compression can be applied between the implanted bone screws to address any asymmetric loss of the disc space height or malalignment.

In some embodiments, facet joint replacement devices may be available in a plurality of different sizes. In such embodiments, after implantation of the tulip head bone screws into the superior and inferior vertebral bodies, a distance is measured between the tulips head portions of the bone screws and a facet joint replacement device can be selected based on the distance measured between the tulip head portions of the bone screws, for example, so that the superior and inferior attachment members of the facet joint replacement device can be securely engaged with the tulip head portions of the implanted bone screws.

In some embodiments, facet joint replacement devices may be available with inferior articulating surfaces and superior articulating surfaces having a plurality of different angular orientations with respect to the sagittal and transverse anatomic planes, as described further herein. In such embodiments, after implantation of the tulip head bone screws into the superior and inferior vertebral body, a facet joint replacement device is selected based on the desired angular orientations of the superior articular surface and inferior articular surface. The desired angular orientations can be selected based on estimated angular orientations of the articular surfaces of a healthy facet joint in the treated motion segment.

In some embodiments, it may desirable for inferior articulating element 104 to reside in a particular position within the enclosing body 106 at the time of implantation into the body. For example, in some embodiments, it is desirable that the inferior articulating element is positioned within the enclosing body 106 so that the inferior articulating surface 126 is at its closest position with respect to the superior articulating surface 128. The position of the inferior articulating element 104 within the enclosing body 106 can be decided based on the position of the spine during implantation of the facet joint replacement device so that the inferior articulating surface 126 and superior articulating surface 128 conform to the natural position of the articular surfaces of the superior and inferior articular process of the spinal motion segment to be treated. FIG. 13 depicts a removable clip 300 according to one embodiment. The removable clip 300 includes a receiving member 302, a receiving member 304, and a connector 306 extending between the receiving member 302 and receiving member 304. The connector 306 prevents relative movement between the receiving member 302 and receiving member 304. The receiving member 302 can be configured to removably secure to the superior attachment member 120. The receiving member 304 can be configured to removably secure to a superior section of the exterior of the enclosing body 106. FIG. 14 depicts the removable clip 300 secured to the facet joint replacement device 100. When the receiving member 302 and receiving member 304 are secured to the facet joint replacement device, the removable clip 300 can constrain relative movement of the inferior articulating body 118 within the enclosing body 106. In some embodiments, the removable clip 300 is metallic.

Methods for implanting the facet joint replacement device 100 can optionally include securing the removable clip 300 to the facet joint replacement device 100 prior to implantation of the facet joint replacement device 100. After the facet joint replacement device 100 is secured to the spine, the removable clip 300 can be removed from the facet joint replacement device to allow for movement of the inferior articulating body 118 within the enclosing body 106.

FIG. 15 depicts a removable clip 310 according to another embodiment. The removable clip 310 includes a receiving member 312, a receiving member 314, and a connector 316 extending between the receiving member 312 and receiving member 314. The connector 316 prevents relative movement between the receiving member 312 and receiving member 314 and is shaped to correspond to the curvature of a side of the facet joint replacement device 100. The receiving member 312 can be configured to removably secure to the superior attachment member 120. The receiving member 314 can be configured to secure to a section of the exterior of the enclosing body 106 near the inferior end. FIG. 16 depicts the removable clip 310 secured to the facet joint replacement device 100. When the receiving member 312 is secured to the superior attachment member 120, the connector 316 extends along a medial side of the enclosing body 106 to the receiving member 314 at the inferior end of the enclosing body 106. The receiving member 314 can be positioned at the inferior end of the enclosing body 106 such that the removable clip 310 is secured to the facet joint replacement device 100. When the removable clip 310 is secured to the facet joint replacement device 100, the removable clip 310 can constrain relative movement of the inferior articulating body 118 within the enclosing body 106. In some embodiments, the removable clip 310 is metallic.

Methods for implanting the facet joint replacement device 100 can optionally include securing the removable clip 310 to the facet joint replacement device 100 prior to implantation of the facet joint replacement device 100. After the facet joint replacement device 100 is secured to the spine, the removable clip 310 can be removed from the facet joint replacement device to allow for movement of the inferior articulating body 118 within the enclosing body 106.

FIG. 17 depicts a posterior perspective view of a facet joint replacement device 400 and a fastener 440 according to another embodiment. The facet joint replacement device 400 includes many of the same or similar components as the facet joint replacement device 100 described with respect to FIGS. 1-7. The facet joint replacement device 400 includes an enclosing element 402 having an enclosing body 406 and an inferior attachment member 412. The facet joint replacement device 400 also includes an inferior articulating element 404 having an articulating body 418 and a superior attachment member 420. The articulating body 418 can include an articulating surface 426, similar to articulating surface 126. A portion of the interior surface of the enclosing body 406 can be shaped to form a superior articulating surface (not shown), similar to articulating surface 128. The enclosing body 406 can include an opening 442 configured to receive the fastener 440. The opening 442 is positioned on a medial section of the enclosing body 406. In some embodiments, the opening 442 is positioned on an inferior section of the enclosing body 406. In some embodiments, the opening 442 is positioned on a superior section of the enclosing body 406. In some embodiments, the opening 442 is positioned mid-position between a superior end of the enclosing body 406 and an inferior end of the enclosing body 406. The articulating body 418 can include a channel 444 configure to align with the opening 442 when in a particular position or range of particular positions within the enclosing body 406 and receive the fastener 440 when aligned with the opening 442. The enclosing body includes a channel 446 configured to align with the channel 444 of the articulating body 418 when the articulating body is aligned with the opening 442. The channel 444 can be configured to receive the fastener 440 when the fastener 440 passes through the opening 442 and channel 444. In some embodiments, the channels 444 and 446 extend along an axis that is the same as, similar to, or parallel to axis 103 as described with respect to FIG. 1B. When the fastener 440 is inserted into the opening 442, channel 444, and/or channel 446, the fastener 440 moves in an inferior, anterior, and lateral direction. If the fastener 440 is removed from the channel opening 442, channel 444, and/or channel 446, the fastener 440 moves in a superior, posterior, and medial direction.

The fastener 440 can include threads configured to be received by complementary threads within the channel 444 and channel 446. In some embodiments, the fastener 440 is a threaded screw. In some embodiments, the fastener 440 is a lag screw. When received within the channel 444 and the channel 446, the fastener 440 can secure the articulating body 418 in a particular position within the enclosing body 406. For example, the fastener 440 can secure the articulating body 418 within the enclosing body 406 so that the inferior articulating surface 426 is at its most proximal position with respect to the superior articulating surface of the enclosing body. By securing the articulating body 418 in a particular position within the enclosing body 406, the fastener 440 can perform a similar function to the removable clip 300.

In some embodiments, methods of implanting the facet joint replacement device 400 include securing the articulating body 418 in a desired position within the enclosing body 406 prior to implantation in the body using the fastener 440. The fastener 440 can be removed after the facet joint replacement device 400 is secured to the spine. In some embodiments, the fastener 440 can remain positioned within the facet joint replacement device 400 following implantation.

In some embodiments, the depth of the fastener 440 within the facet joint replacement device 400 can be altered by rotating the fastener 440. In some embodiments, changing the depth of the fastener 440 within the facet joint replacement device can change the distance between the inferior articulating surface 426 and the superior articulating surface of the enclosing body 406. In some embodiments, the depth of the fastener 440 can be changed after implantation to provide a different distance between the inferior articulating surface 426 and the superior articulating surface of the enclosing body 406. In some embodiments, the fastener 440 can allow for at least some movement between the inferior articulating surface 426 and superior articulating surface of the enclosing body at least some depths of the fastener 440.

Figure 18:
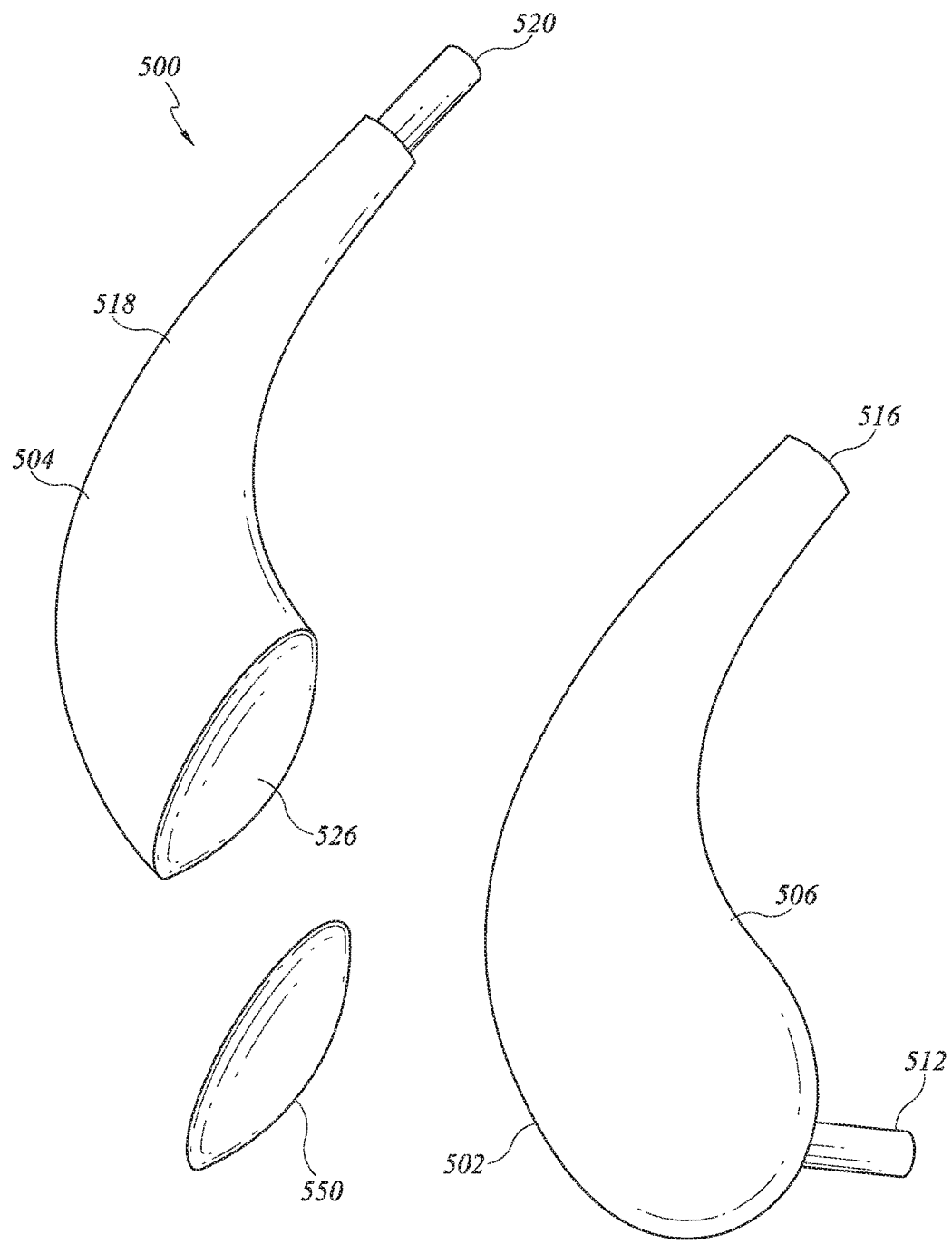
FIG. 18 depicts an exploded view of a facet joint replacement device 500.

FIG. 18 depicts an exploded view of a facet joint replacement device 500 in accordance with another embodiment. The facet joint replacement device 500 includes many of the same or similar components as the facet joint replacement device 100 described with respect to FIGS. 1A-7. The facet joint replacement device 500 includes an enclosing element 502 having an enclosing body 506, an inferior attachment member 512, and an opening 516. The facet joint replacement device 500 also includes an inferior articulating element 504 having an articulating body 518 and a superior attachment member 520. The articulating body 518 can include an inferior articulating surface 526, similar to inferior articulating surface 126. The inferior articulating surface 526 can be convex. A portion of the interior surface of the enclosing body 506 can be shaped to form a superior articulating surface (not shown), similar to articulating surface 128. The superior articulating surface of the facet joint replacement device 500 can be concave. The facet joint replacement device 500 further includes a veneer 550 configured to be positioned between the inferior articulating surface 526 and the superior articulating surface of the facet joint replacement device 500. In some embodiments, the veneer has a thickness of 1 mm, 2 mm, 3 mm, 4 mm, 5 mm, between 1 mm and 3 mm, between 1 mm and 2 mm, or between 2 mm and 3 mm. The veneer 550 can include a low friction material, such as high molecular weight polyethelyne. In some embodiments, the veneer is formed of vitamin E impregnated polyethylene, which may function as a free radical scavenger. The veneer 550 can reduce friction and wear between the inferior articulating surface 526 and the superior articulating surface of the facet joint replacement device 500. In some embodiments, the veneer 550 includes a concave side configured to engage the inferior articulating surface 526. The veneer 550 can also include a convex side configured to engage the superior articulating surface of the facet joint replacement device 500. In some embodiments, the veneer 550 can be secured to the inferior articulating surface 526. In some embodiments, the veneer 550 can be secured to the inferior articulating surface 526 by a fastener, such as a screw. In an alternative embodiment, the veneer 550 can be formed as part of a sleeve configured to fit over at least a portion of the articulating body 518 including the inferior articulating surface 526.

Figure 19:
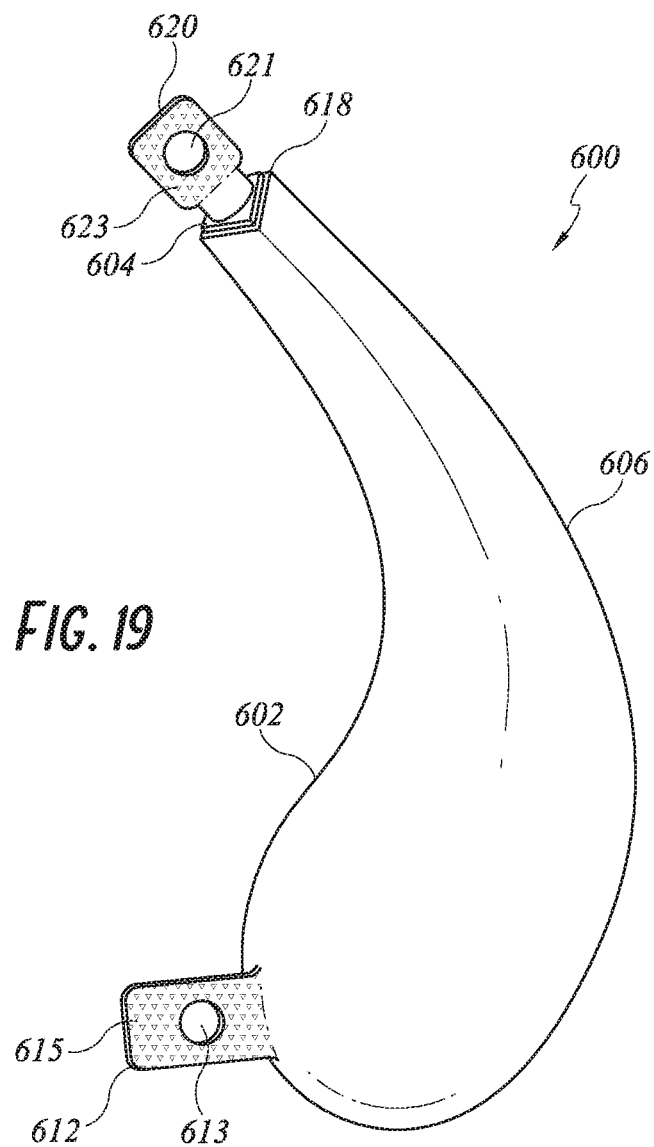
FIG. 19 depicts a posterior perspective view of a facet joint replacement device 600.

FIG. 19 depicts a posterior view of a facet joint replacement device 600 according to another embodiment. The facet joint replacement device 600 includes many of the same or similar components as the facet joint replacement device 100 described with respect to FIGS. 1A-7. The facet joint replacement device 600 includes an enclosing element 602 having an enclosing body 606 and an inferior attachment member 612. The facet joint replacement device 600 also includes an inferior articulating element 604 having an articulating body 618 and a superior attachment member 620. The articulating body 618 can include an articulating surface (not shown), similar to articulating surface 126. A portion of the interior surface of the enclosing body 606 can be shaped to form a superior articulating surface (not shown), similar to articulating surface 128. The inferior attachment member 612 includes a hole 613 and a textured surface 615. The superior attachment member 620 includes a hole 621 and a textured surface 623. The holes 613 and 621 can each receive a fastener, such as a threaded bone screw, to secure the facet joint replacement device 600 to the spine.

The shape of the inferior attachment member 612 allows for alignment of the inferior attachment member 612 with a superior attachment member of a facet joint replacement device positioned to replace a facet joint at an inferior contiguous vertebral body. The shape of the superior attachment member 620 allows for alignment of the superior attachment member 620 with an inferior attachment member of a facet joint replacement device positioned to replace a facet joint of a superior contiguous vertebral body.

Figure 20:
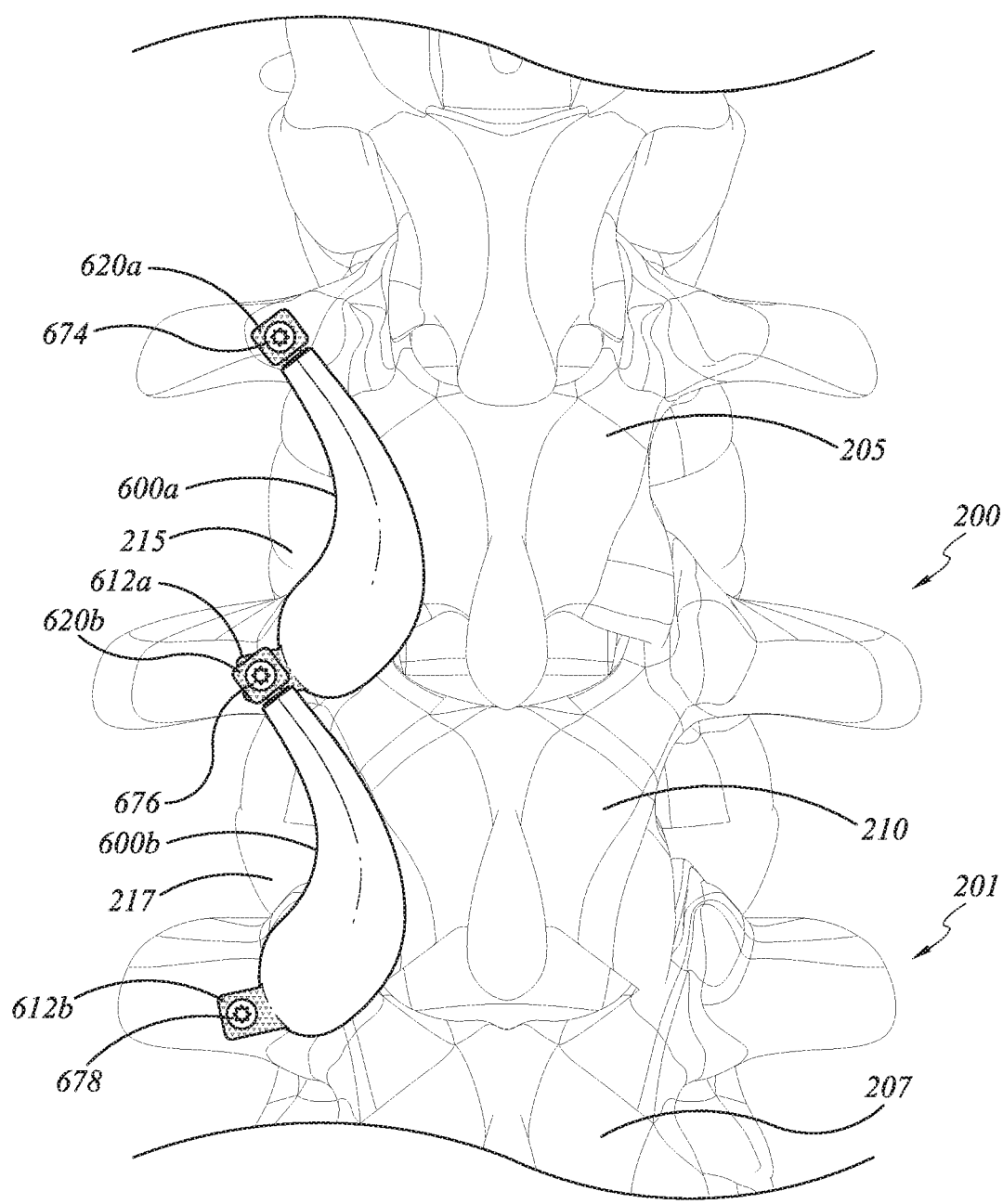
FIG. 20 depicts a posterior view of the motion segment 200 and a motion segment 201 with a first facet joint replacement device 600A and a second facet joint replacement device 600B implanted ipsilaterally.

FIG. 20 depicts a posterior view of the motion segment 200 and a motion segment 201 with a facet joint replacement device 600A and a facet joint replacement device 600B implanted ipsilaterally. The facet joint replacement device 600A is positioned to replace the facet joint 260 of the motion segment 200. The facet joint replacement device 600B is positioned to replace a facet joint of the motion segment 201, which is inferior to motion segment 200 and includes vertebral body 210, vertebral body 207, and intervertebral disc 217. The facet joint replacement devices 600A and 600B include the same components as the facet joint replacement device 600 described herein. The facet joint replacement device 600A includes a superior attachment member 620A and an inferior attachment member 612A, each having a hole and a textured surface. The facet joint replacement device 600B includes a superior attachment member 620B and an inferior attachment member 612B, each having a hole and a textured surface. The superior attachment member 620A is secured to the superior vertebral body 205 by a fastener 674 passing through the hole of the superior attachment member 620A. The inferior attachment member 612A is positioned so that the hole of the inferior attachment member 612A aligns with the hole of the superior attachment member 620B. The textured surfaces of the attachment members 612A and 620B can contact one another to provide friction or otherwise constrain movement of the attachment members 612A and 620B relative to one another once aligned. A fastener 676 extends through both the hole in the attachment member 612A and the hole in the attachment member 620B to secure the attachment members 612A and 620B to the inferior vertebral body 210. A fastener 678 extends through the hole of the inferior attachment member 612B to secure the attachment member 612B to vertebral body 207. In some embodiments, each of the fasteners 674, 676, and 678 can include a bone screw and/or a threaded locking nut.

Methods of implanting facet joint replacement devices 600A and 600B can include aligning the opening of the inferior attachment member 612A with the opening of the superior attachment member 620B and securing the inferior attachment member 612A and the superior attachment member 620B to the same vertebral body by extending a fastener through the opening of the inferior attachment member 612A device and the opening of the superior attachment member 620B.

FIG. 21 depicts a removable clip 320 according to another embodiment. The removable clip 320 includes a hook member 322, a receiving member 324, and a connector 326 extending between the hook member 322 and receiving member 324. The connector 326 prevents relative movement between the receiving member 322 and receiving member 324 and is shaped to correspond to the curvature of the posterior of the facet joint replacement device 600. The hook member 322 can be configured to removably secure to the superior attachment member 620. The receiving member 324 can be configured to secure to a section of the exterior of the enclosing body 606 near the inferior end. FIG. 22 depicts the removable clip 320 secured to the facet joint replacement device 600. When the hook member 322 is secured to the superior attachment member 620, the connector 326 extends along a posterior section of the enclosing body 606 to the receiving member 324 at the inferior end of the enclosing body 606. The receiving member 324 can be positioned at the inferior end of the enclosing body 606 such that the removable clip 320 is secured to the facet joint replacement device 600. When the removable clip 320 is secured to the facet joint replacement device 600, the removable clip 320 can constrain relative movement of the inferior articulating body 618 within the enclosing body 606. In some embodiments, the removable clip 320 is metallic.

Methods for implanting the facet joint replacement device 600 can optionally include securing the removable clip 320 to the facet joint replacement device 600 prior to implantation of the facet joint replacement device 600. After the facet joint replacement device 600 is secured to the spine, the removable clip 320 can be removed from the facet joint replacement device to allow for movement of the inferior articulating body 618 within the enclosing body 606.

While this invention has been particularly shown and described with reference to embodiments thereof, it will be understood by those skilled in the art that various changes in form and details may be made therein without departing from the scope of the invention. For all of the embodiments described above, the steps of the methods need not be performed sequentially.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, 0.1 degree, or otherwise.

It will be apparent to those skilled in the art that various modifications and variations can be made in the present invention without departing from the scope or spirit of the invention. Thus, it is intended that the present invention cover modifications and variations of this invention.

What is claimed is:

1. A facet joint replacement system, comprising:
    a facet joint replacement device comprising:
        an enclosing element comprising:
            an enclosing body comprising:
                a superior end having an opening;
                an inferior end; and
                an inner cavity defined by an interior surface of the enclosing body, wherein a portion of the interior surface of the enclosing body forms a superior articulating surface, wherein the inner cavity narrows between the superior articulating surface and the superior end of the enclosing body; and
            an inferior attachment member extending from the inferior end of the enclosing body, the inferior attachment member configured to be fixed with respect to an inferior vertebral body; and
        an inferior articulating element comprising:
            an articulating body positioned within the inner cavity of the enclosing body of the enclosing element, the articulating body configured to move within the inner cavity of the enclosing body of the enclosing element, wherein the articulating body comprises:
                a superior end;
                an inferior end forming an inferior articulating surface; and
            a superior attachment member extending from the superior end of the articulating body and superior to the opening of the superior end of the enclosing body, the superior attachment member configured to be fixed with respect to a superior vertebral body.

2. The facet joint replacement system of claim 1, wherein the enclosing body of the enclosing element tapers from the inferior end of the enclosing body to the superior end of the enclosing body.

3. The facet joint replacement system of claim 1, wherein the articulating body of the inferior articulating element tapers from the inferior end of the articulating body to the superior end of the articulating body.

4. The facet joint replacement system of claim 1, wherein the enclosing body of the enclosing element bows medially between the superior articulating surface and the superior end of the enclosing body.

5. The facet joint replacement system of claim 1, wherein the articulating body of the inferior articulating element bows medially between the inferior articulating surface and the superior end of the articulating body.

6. The facet joint replacement system of claim 1, wherein the inferior attachment member and superior attachment member each comprise an attachment rod.

7. The facet joint replacement system of claim 1, wherein the inferior attachment member and superior attachment member each comprise a hole configured to receive a fastener.

8. The facet joint replacement system of claim 1, wherein the inferior articulating surface of the articulating body is configured to translate relative to the superior articulating surface of the enclosing body along an axis extending through the inferior articulating surface and the superior articulating surface.

9. The facet joint replacement system of claim 1, wherein one or both of the enclosing element and the inferior articulating element comprise one or more metals or metal alloys.

10. The facet joint replacement system of claim 9, wherein the one or more metals or metal alloys comprise on or more of cobalt-chromium and titanium based alloys.

11. The facet joint replacement system of claim 1, wherein movement of the articulating body of the inferior articulating element is constrained in at least one direction within the inner cavity of the enclosing body of the enclosing element.

12. The facet joint replacement system of claim 1, wherein one or both of the enclosing element and the inferior articulating element comprise a ceramic.

13. The facet joint replacement system of claim 1, wherein the inferior articulating surface of the articulating body is convex.

14. The facet joint replacement system of claim 1, wherein the superior articulating surface of the enclosing body is concave.

15. The facet joint replacement system of claim 1, wherein at least a portion of the interior surface of the enclosing body comprises one or more grooves, wherein at least a portion of articulating body comprises one or more edges configured to slide within the one or more grooves of the interior surface of the enclosing body.

16. The facet joint replacement system of claim 15, wherein the one or more grooves of the interior surface of the enclosing body are shaped to constrain rotational motion of the articulating body within the enclosing body.

17. The facet joint replacement system of claim 1, further comprising a veneer positioned between the inferior articulating surface of the articulating body and the superior articulating surface of the enclosing body.

18. The facet joint replacement system of claim 17, wherein the veneer comprises a low friction material.

19. The facet joint replacement system of claim 17, wherein the veneer comprises high molecular weight polyethylene.

20. The facet joint replacement system of claim 17, wherein the veneer comprises a concave side configured to engage the inferior articulating surface of the articulating body and a convex side configured to engage the superior articulating surface of the enclosing body.

21. The facet joint replacement system of claim 1, further comprising:
    an inferior fastener configured to secure the inferior attachment member to the inferior vertebral body;
    a superior fastener configured to secure the superior attachment member to the superior vertebral body.

22. The facet joint replacement system of claim 21, wherein one or more of the inferior fastener and the superior fastener comprise a tulip head bone screw.

23. The facet joint replacement system of claim 1, wherein the facet joint replacement device comprises a first facet joint replacement device, wherein the system further comprises a second facet joint replacement device, wherein an opening of the inferior attachment member of the first facet joint replacement device is configured to align with an opening of a superior attachment member of the second facet joint replacement device.

24. A method of implanting a facet joint replacement system utilizing the facet joint replacement device of claim 1, comprising:
    securing the superior attachment member to the superior vertebral body; and
    securing the inferior attachment member to the inferior vertebral body.

25. The method of claim 24, further comprising:
    engaging a removable clip to the superior attachment member and a portion of the enclosing body prior to securing the superior attachment member to the superior vertebral body and securing the inferior attachment member to the inferior vertebral body to constrain movement of the articulating body within the enclosing body; and
    removing the removable clip after securing the superior attachment member to the superior vertebral body and securing the inferior attachment member to the inferior vertebral body.

26. The method of claim 24, wherein the facet joint replacement device comprises a first facet joint replacement device, further comprising:
    providing a second facet joint replacement device;
    aligning an opening of the inferior attachment member of the first facet joint replacement device with an opening of the superior attachment member of the second facet joint replacement device; and
    securing the inferior attachment member of the first facet joint replacement device and the superior attachment member of the second facet joint replacement device to the same vertebral body by extending a fastener through the opening of the inferior attachment member of the first facet joint replacement device and the opening of the superior attachment member of the second facet joint replacement device.

27. A facet joint replacement system, comprising:
    a facet joint replacement device comprising:
        an enclosing element comprising:
            an enclosing body comprising:
                a superior end having an opening;
                an inferior end; and
                an inner cavity defined by an interior surface of the enclosing body, wherein a portion of the interior surface of the enclosing body forms a superior articulating surface; and
            an inferior attachment member extending from the inferior end of the enclosing body, the inferior attachment member configured to be fixed with respect to an inferior vertebral body;
        an inferior articulating element comprising:
            an articulating body positioned within the inner cavity of the enclosing body of the enclosing element, the articulating body configured to move within the inner cavity of the enclosing body of the enclosing element, wherein the articulating body comprises:
                a superior end;
                an inferior end forming an inferior articulating surface; and
            a superior attachment member extending from the superior end of the articulating body and superior to the opening of the superior end of the enclosing body, the superior attachment member configured to be fixed with respect to a superior vertebral body; and
        a removable clip configured to engage the superior attachment member of the inferior articulating element and either the superior end of the enclosing body or the inferior end of the enclosing body to constrain movement of the articulating body within the enclosing body.

28. A facet joint replacement system, comprising:
    a facet joint replacement device comprising:
        an enclosing element comprising:
            an enclosing body comprising:
                a superior end having an opening;
                an inferior end; and
                an inner cavity defined by an interior surface of the enclosing body, wherein a portion of the interior surface of the enclosing body forms a superior articulating surface; and
            an inferior attachment member extending from the inferior end of the enclosing body, the inferior attachment member configured to be fixed with respect to an inferior vertebral body;
        an inferior articulating element comprising:
            an articulating body positioned within the inner cavity of the enclosing body of the enclosing element, the articulating body configured to move within the inner cavity of the enclosing body of the enclosing element, wherein the articulating body comprises:
                a superior end;
                an inferior end forming an inferior articulating surface; and
            a superior attachment member extending from the superior end of the articulating body and superior to the opening of the superior end of the enclosing body, the superior attachment member configured to be fixed with respect to a superior vertebral body; and
        a fastener;
    wherein the articulating body comprises a first channel extending through at least a portion of the inferior articulating body and the inferior articulating surface, wherein the enclosing body comprises a second channel extending through at least a portion of the superior articulating surface, wherein the fastener extends through the first channel and the second channel.

29. A method of replacing a facet joint, comprising:
resecting at least a portion of a facet joint defined by an articular process of a superior vertebral body and an articular process of an inferior vertebral body;
cannulating a pedicle of the inferior vertebral body and a pedicle of the superior vertebral body;
inserting a first fastener into the pedicle of the inferior vertebral body and a second fastener into the pedicle of the superior vertebral body; and
securing a facet joint replacement device to the first fastener and the second fastener, the facet joint replacement device comprising:
an enclosing body;
an inferior articulating surface enclosed within the enclosing body; and
a superior articulating surface enclosed within the enclosing body.

30. The method of claim 29, further comprising introducing the facet joint replacement device into a body of a patient while the inferior articulating surface is positioned within the enclosing body.

31. The method of claim 29, wherein resecting at least a portion of the facet joint comprises fully resecting the facet joint.

* * * * *